(12) United States Patent
Thielen et al.

(10) Patent No.: US 8,029,461 B2
(45) Date of Patent: Oct. 4, 2011

(54) CLOSABLE LOOP ACCESS GUIDE CATHETER

(76) Inventors: Joseph Michael Thielen, Buffalo, MN (US); William Joseph Drasler, Minnetonka, MN (US)

(*) Notice: Subject to any disclaimer, the term of this patent is extended or adjusted under 35 U.S.C. 154(b) by 211 days.

(21) Appl. No.: 12/319,641

(22) Filed: Jan. 9, 2009

(65) Prior Publication Data
US 2009/0182268 A1 Jul. 16, 2009

Related U.S. Application Data

(60) Provisional application No. 61/010,753, filed on Jan. 11, 2008, provisional application No. 61/065,919, filed on Feb. 15, 2008, provisional application No. 61/067,879, filed on Mar. 3, 2008, provisional application No. 61/070,398, filed on Mar. 21, 2008, provisional application No. 61/190,088, filed on Aug. 26, 2008.

(51) Int. Cl.
*A61M 31/00* (2006.01)
(52) U.S. Cl. ............... 604/95.04
(58) Field of Classification Search ............... 604/95.04
See application file for complete search history.

(56) References Cited

U.S. PATENT DOCUMENTS

| 6,048,329 A * | 4/2000 | Thompson et al. ....... 604/95.04 |
| 2005/0143770 A1 * | 6/2005 | Carter et al. ............... 606/170 |

* cited by examiner

*Primary Examiner* — Nicholas D Lucchesi
*Assistant Examiner* — Jason Flick

(57) ABSTRACT

The Access guide catheter provides passage for therapeutic and diagnostic devices through vessels or conduits that return substantially in a direction from which they originated. One application is for delivery of therapeutic catheters to the carotid or cerebral arteries via access from the radial or brachial artery. The guide catheter enters the aorta from one of the great vessels, forms a closed loop in the aorta, and is directed back into a great vessel in an opposed direction. The distal portion of the guide catheter is advanced into the great vessel for support. Further support is attained by providing tension to the proximal shaft of the guide catheter. Flexibility of the guide catheter allows diagnostic angiograms to be performed prior to delivery of a therapeutic catheter or device.

13 Claims, 26 Drawing Sheets

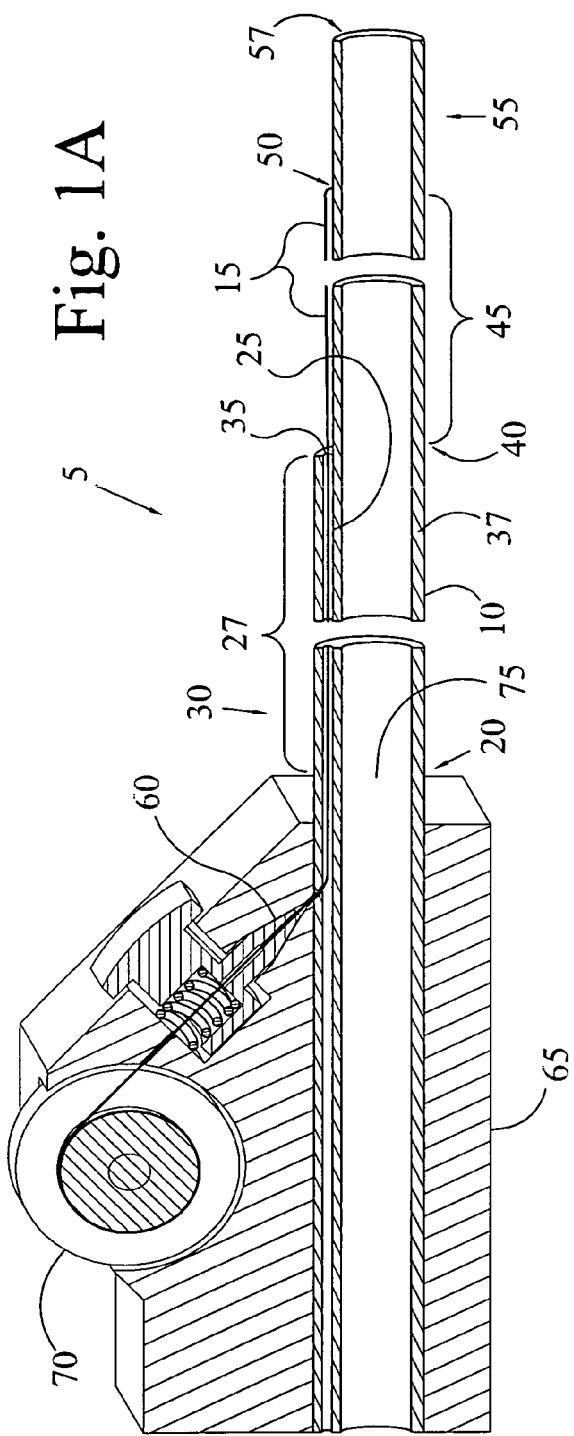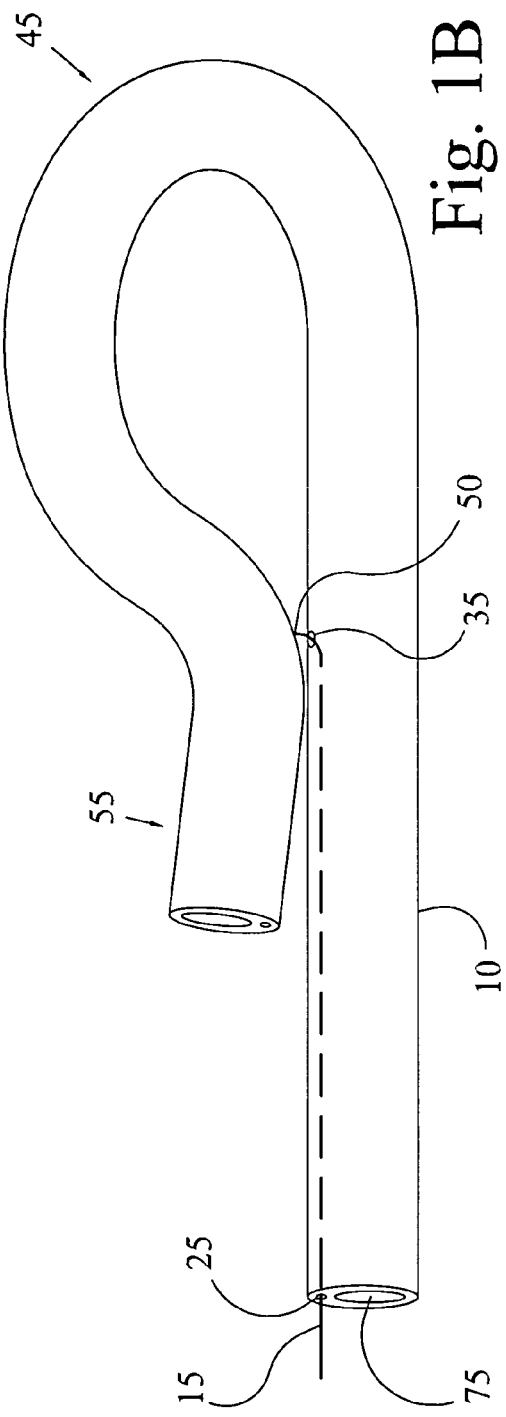

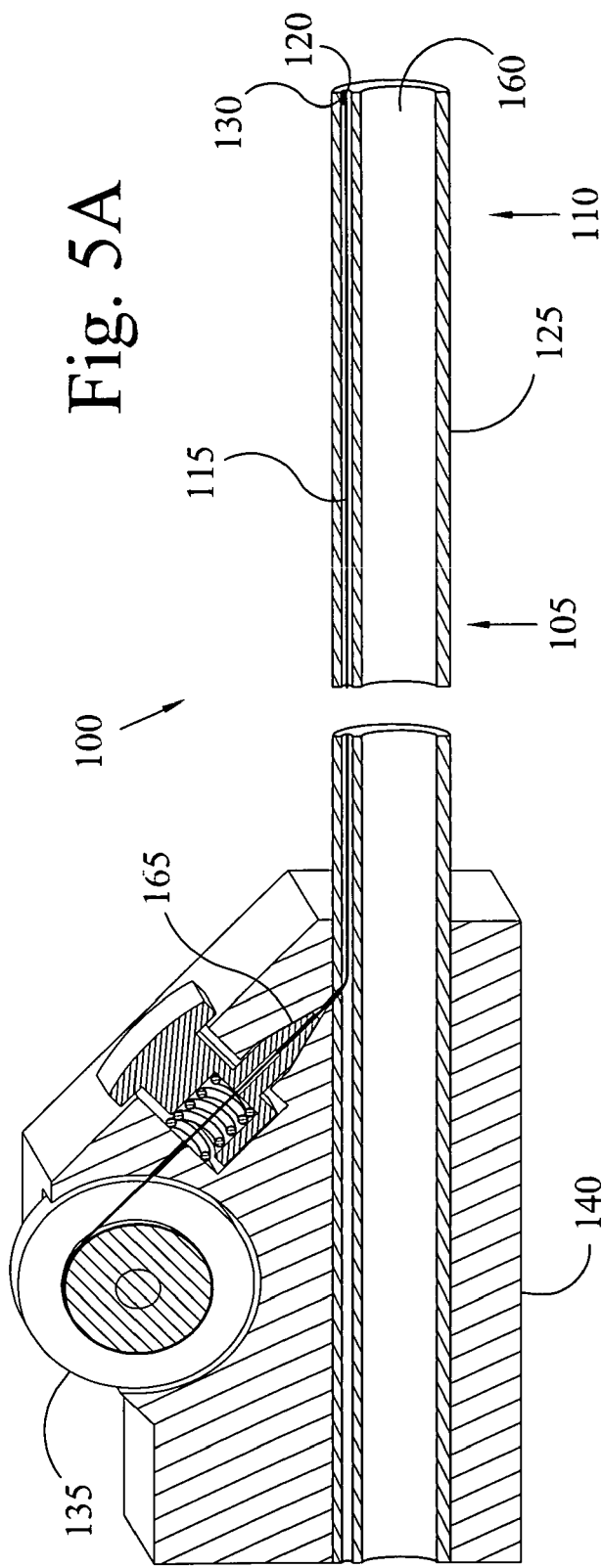
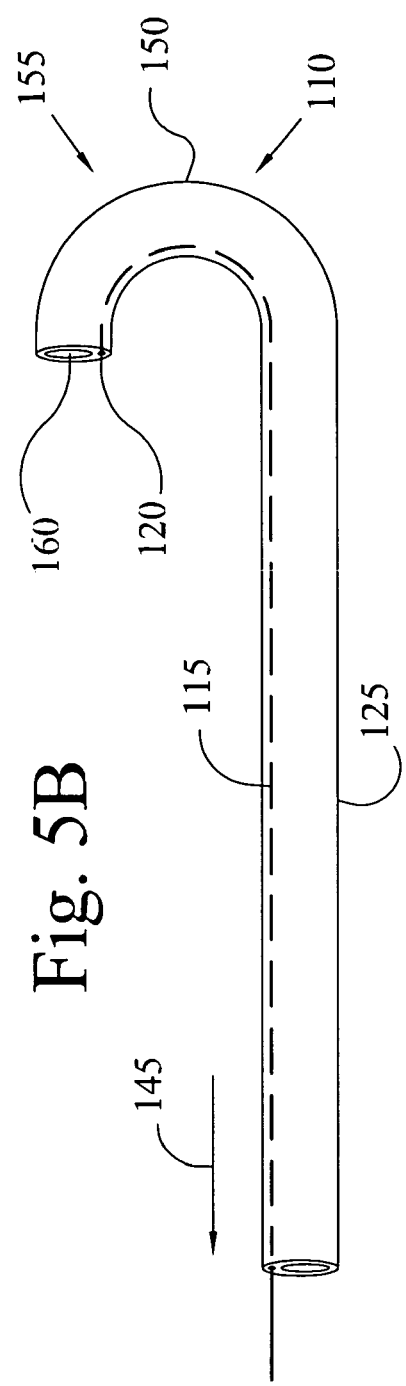
Fig. 5A
Fig. 5B

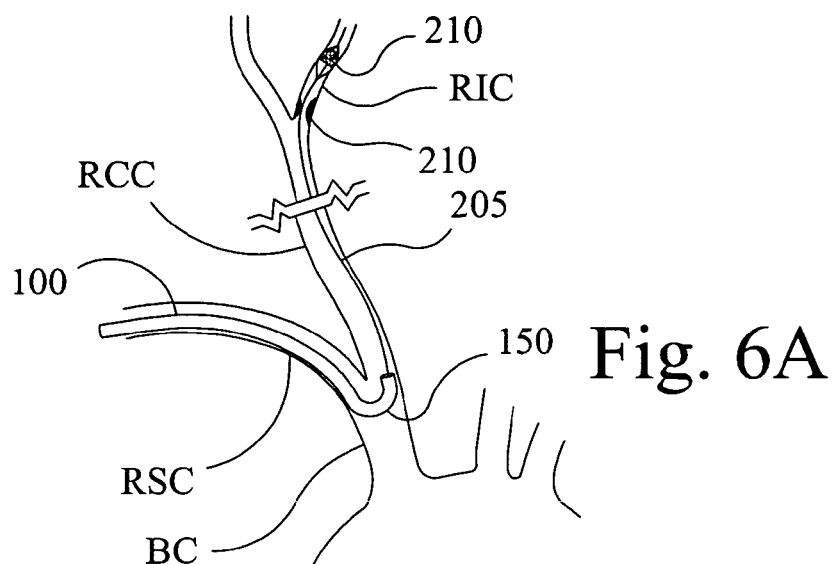
Fig. 6A
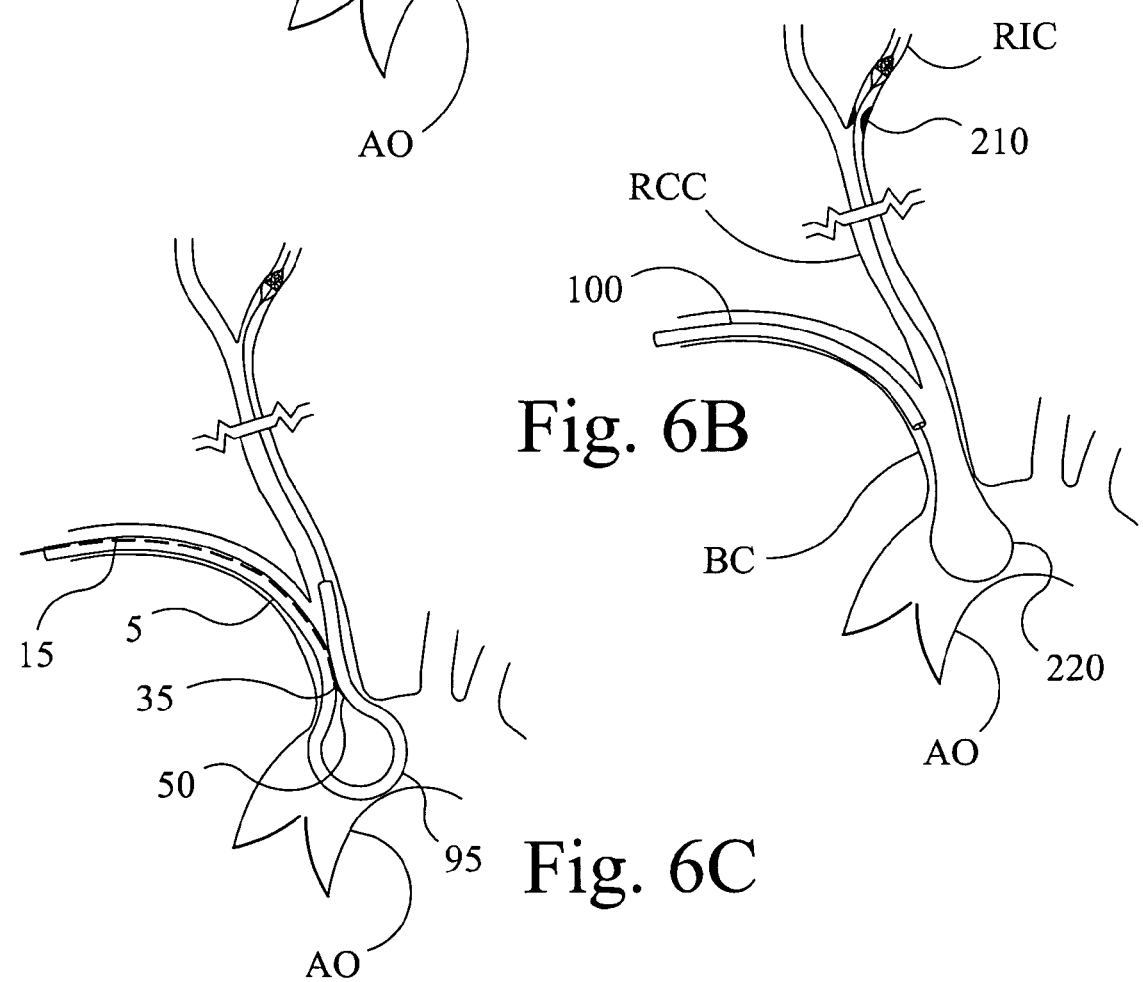
Fig. 6B
Fig. 6C

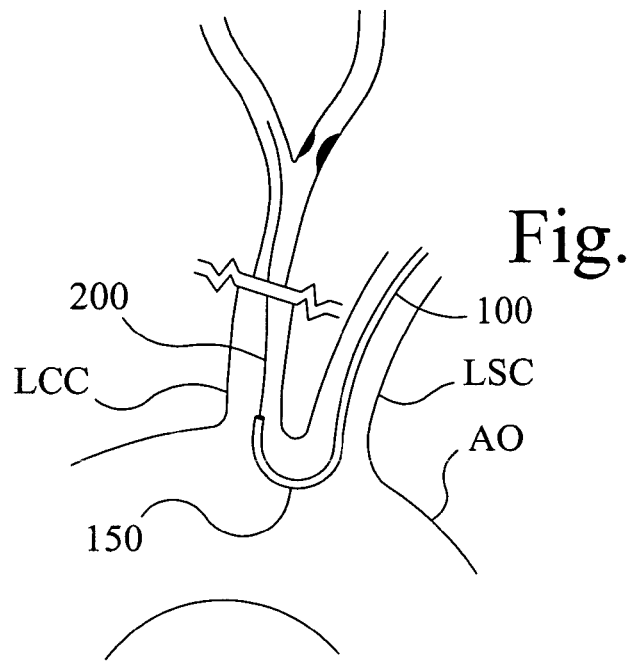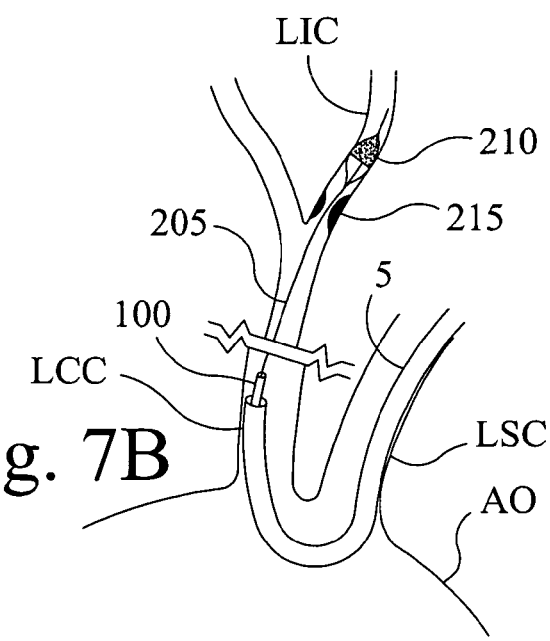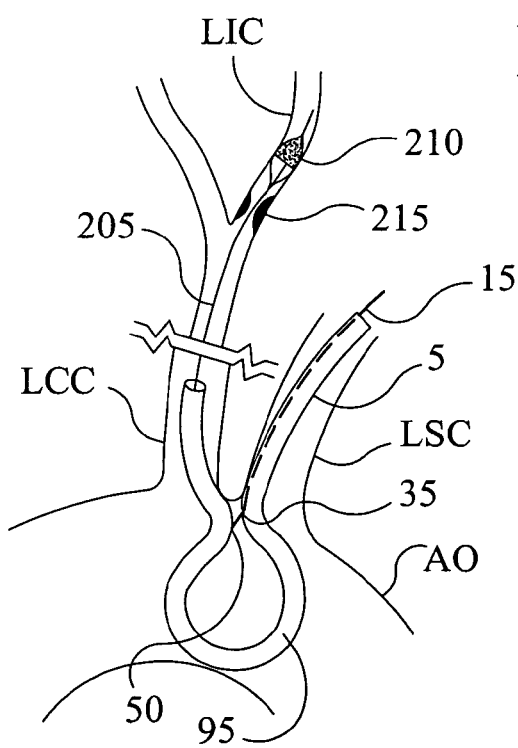

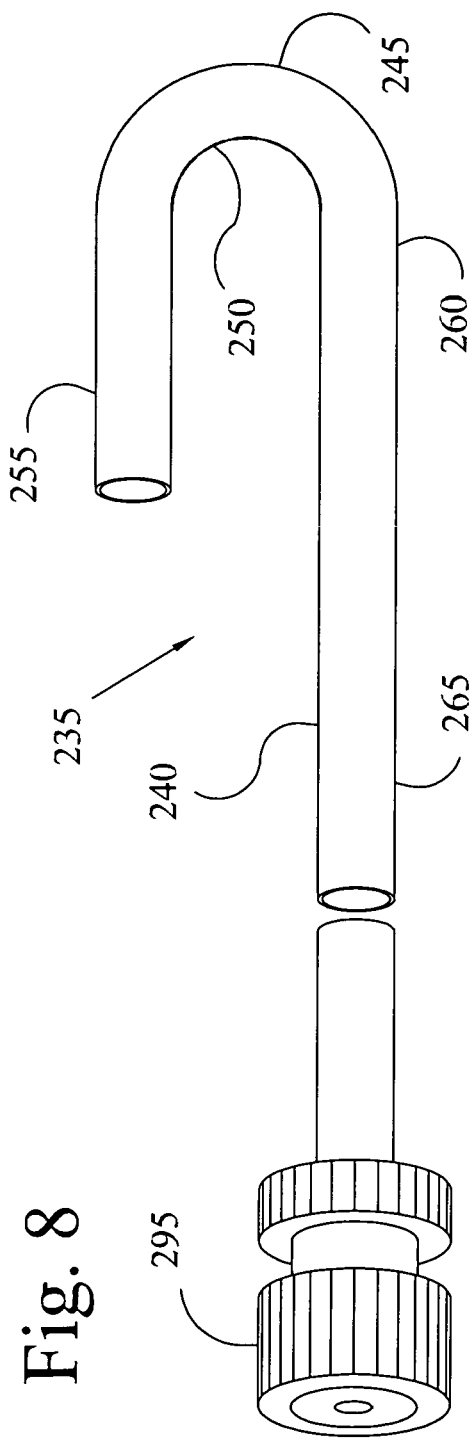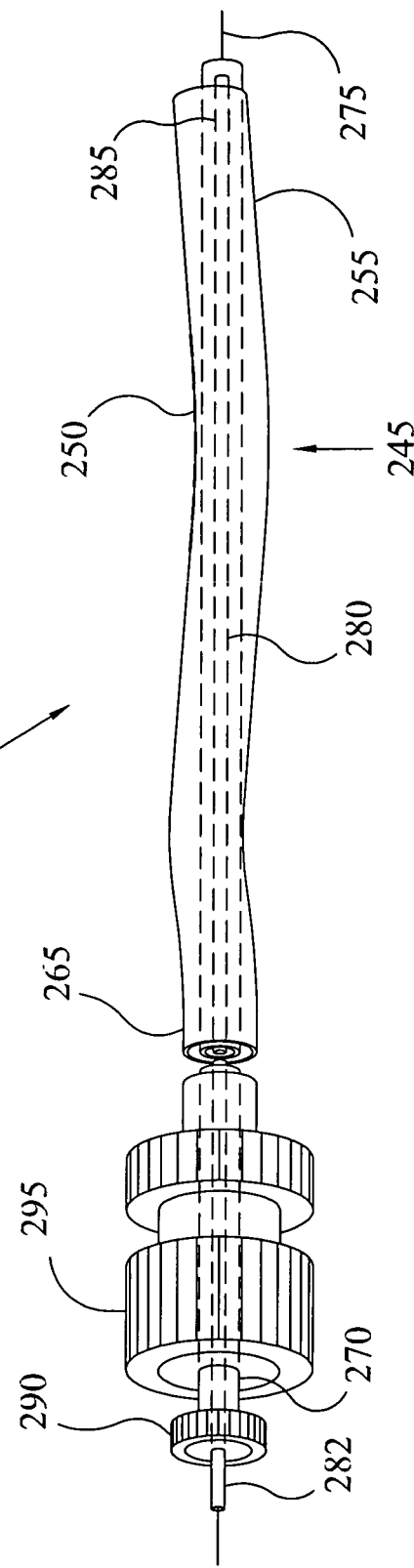

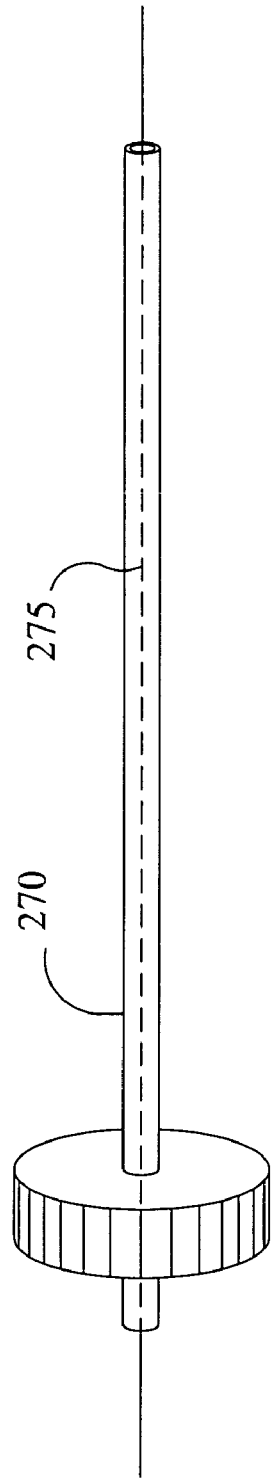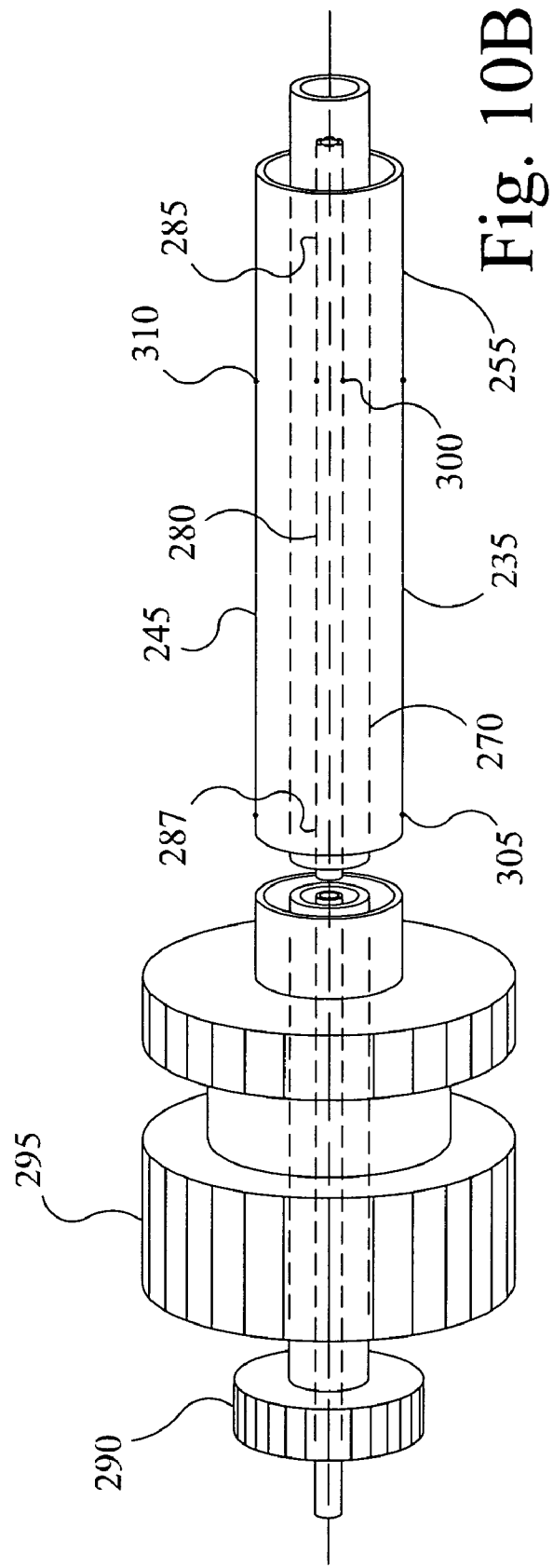

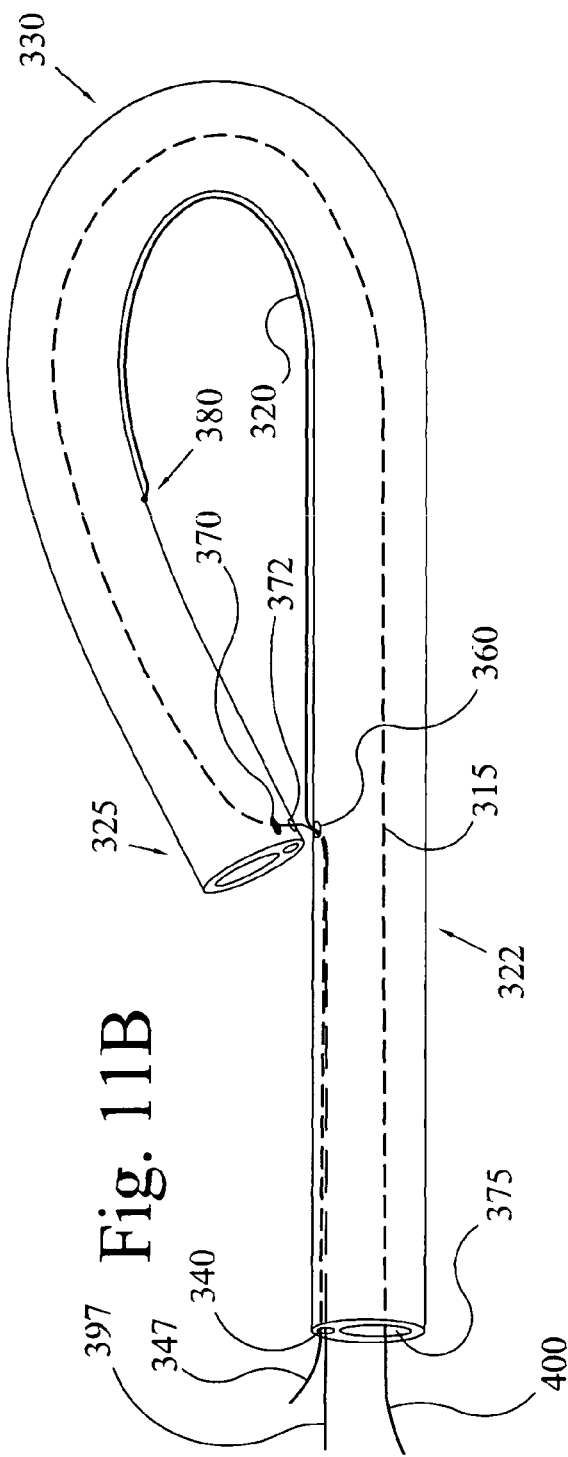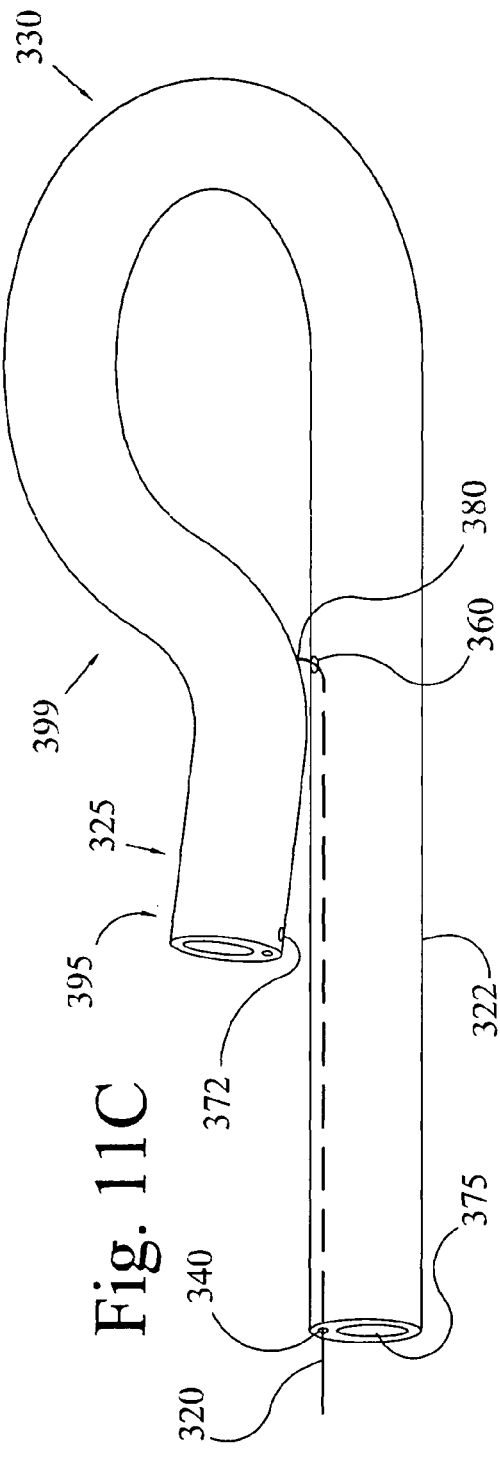

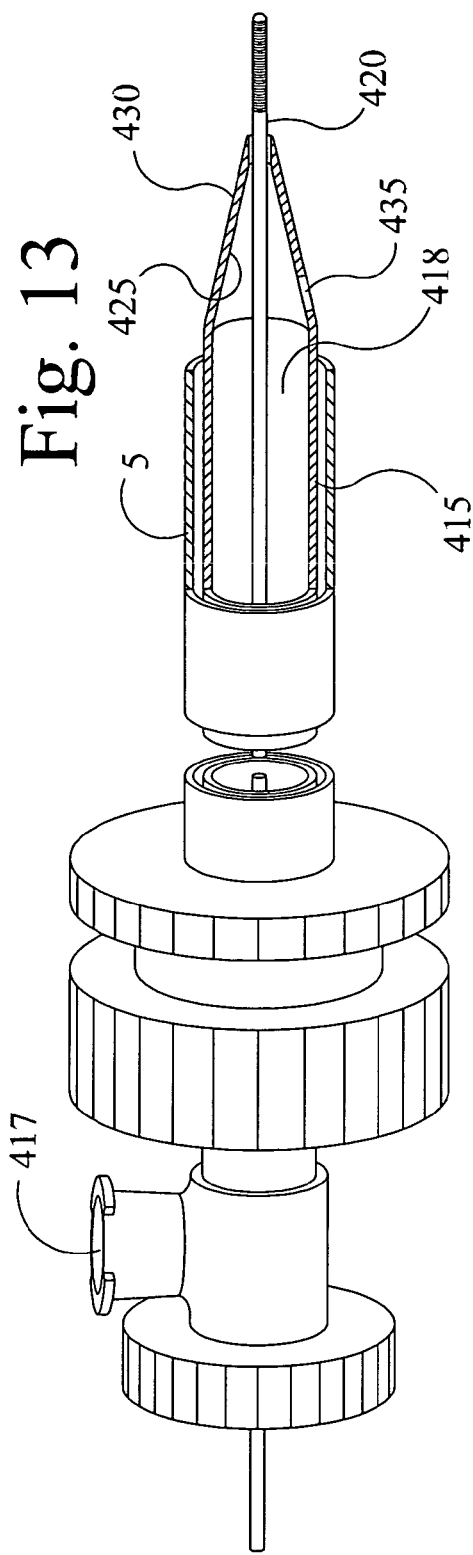
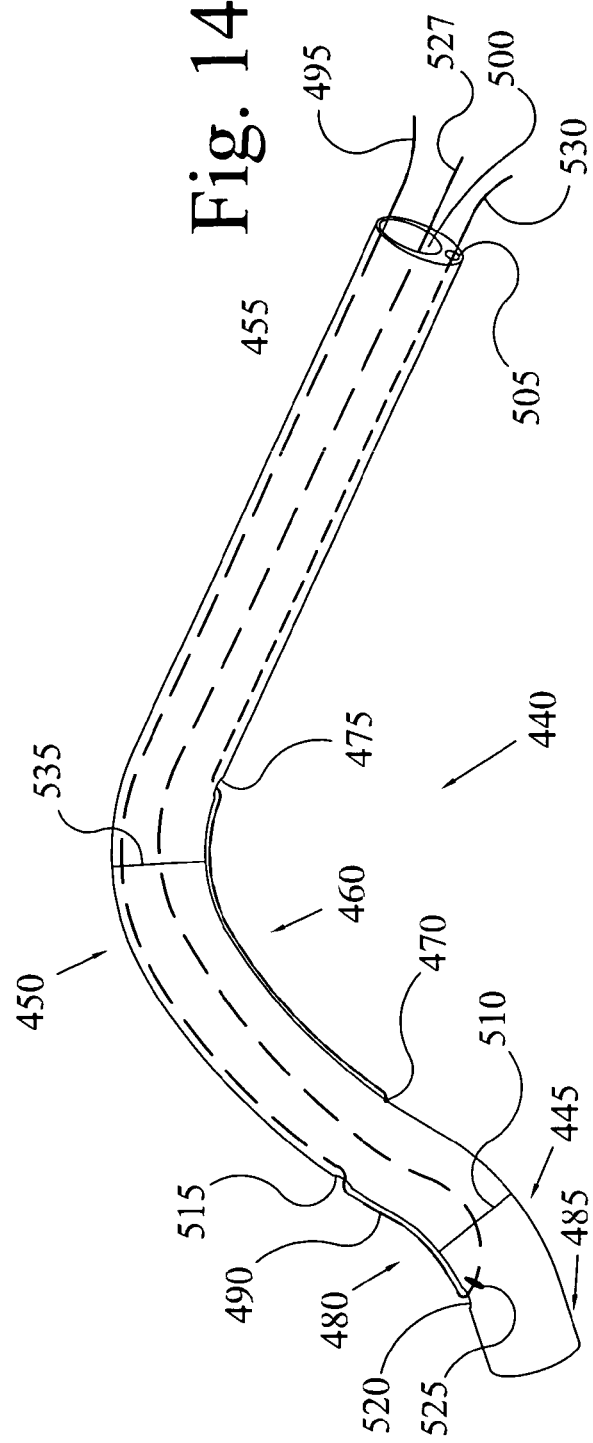

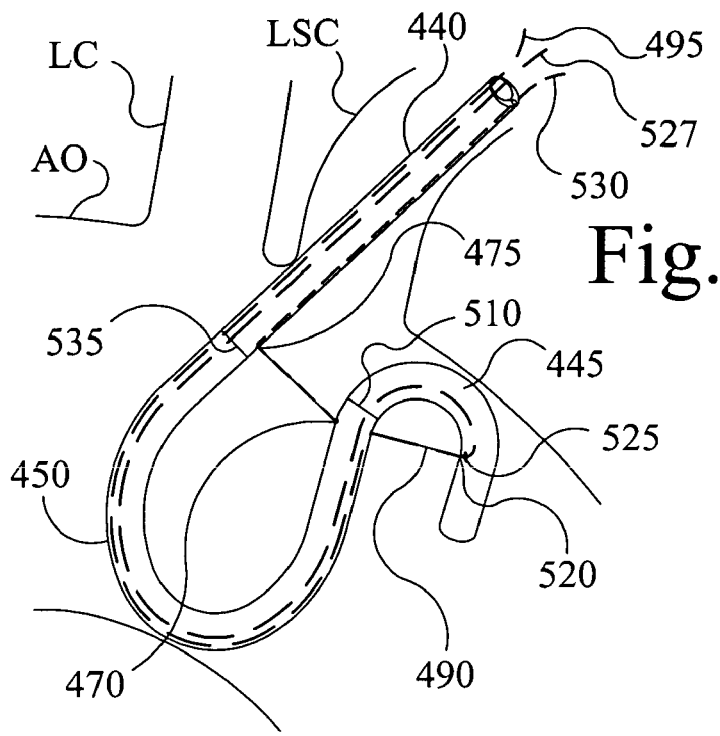
Fig. 15
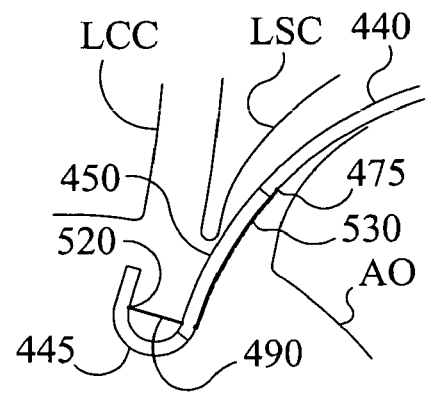
Fig. 16A
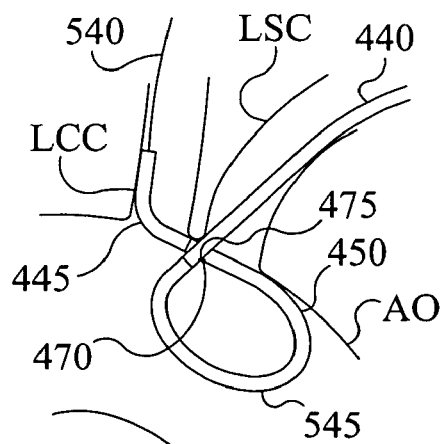
Fig. 16C
Fig. 16B

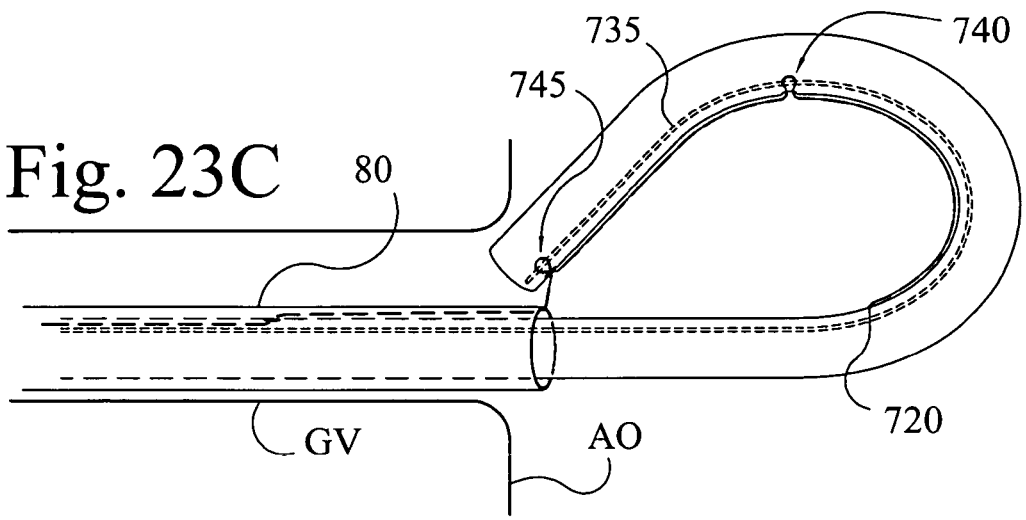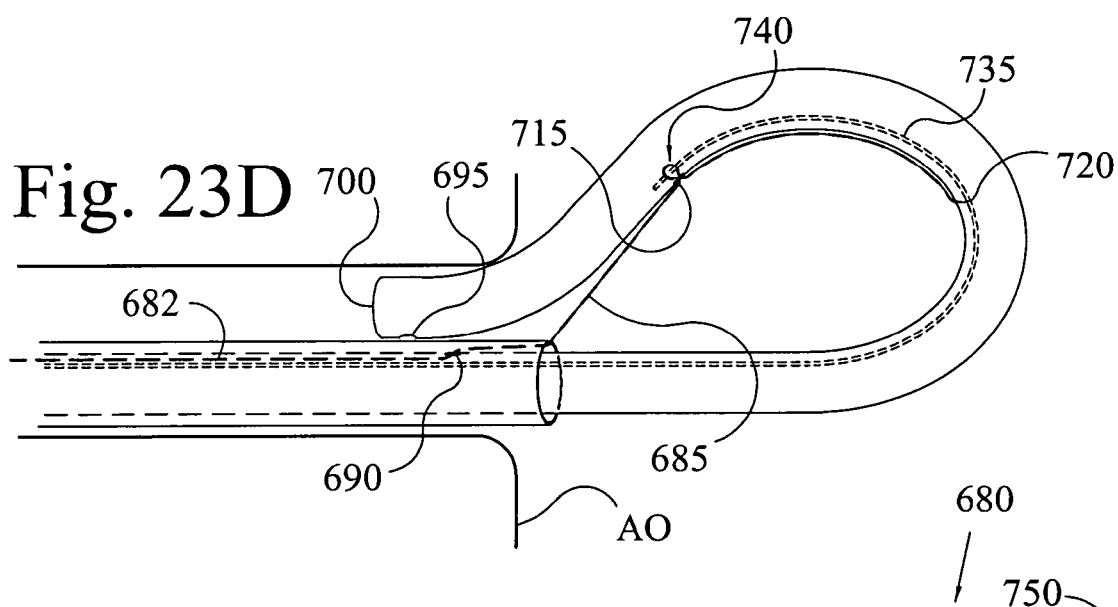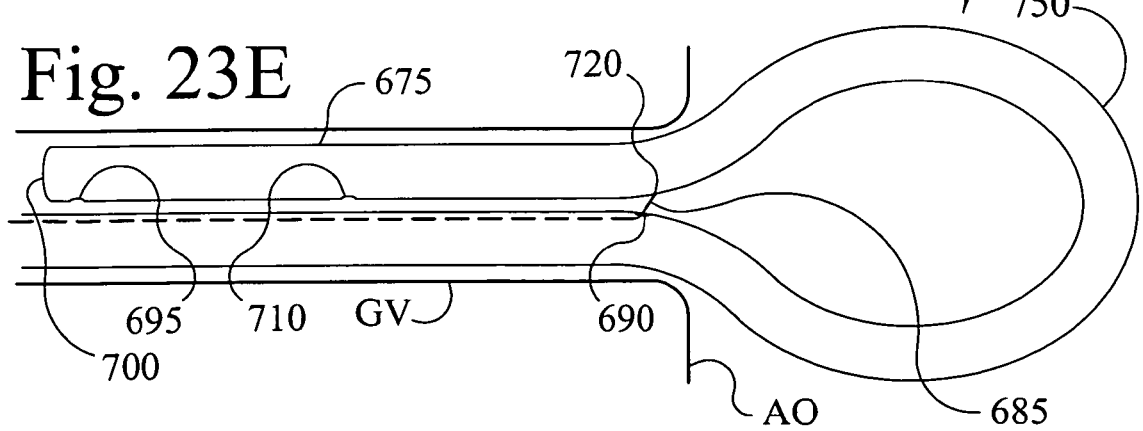

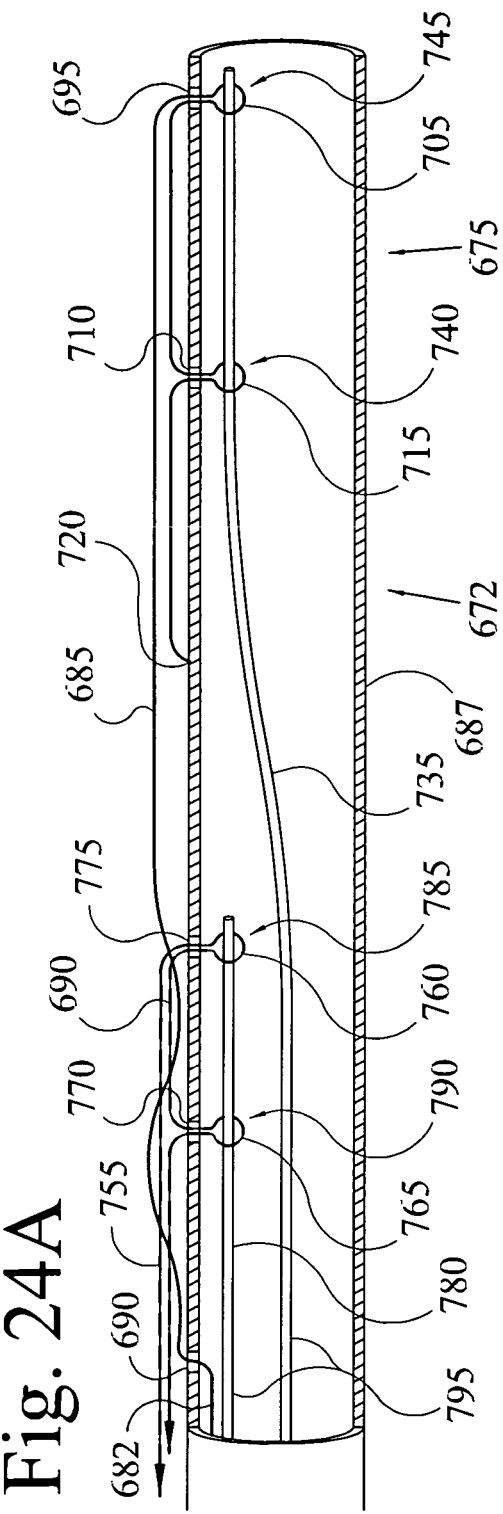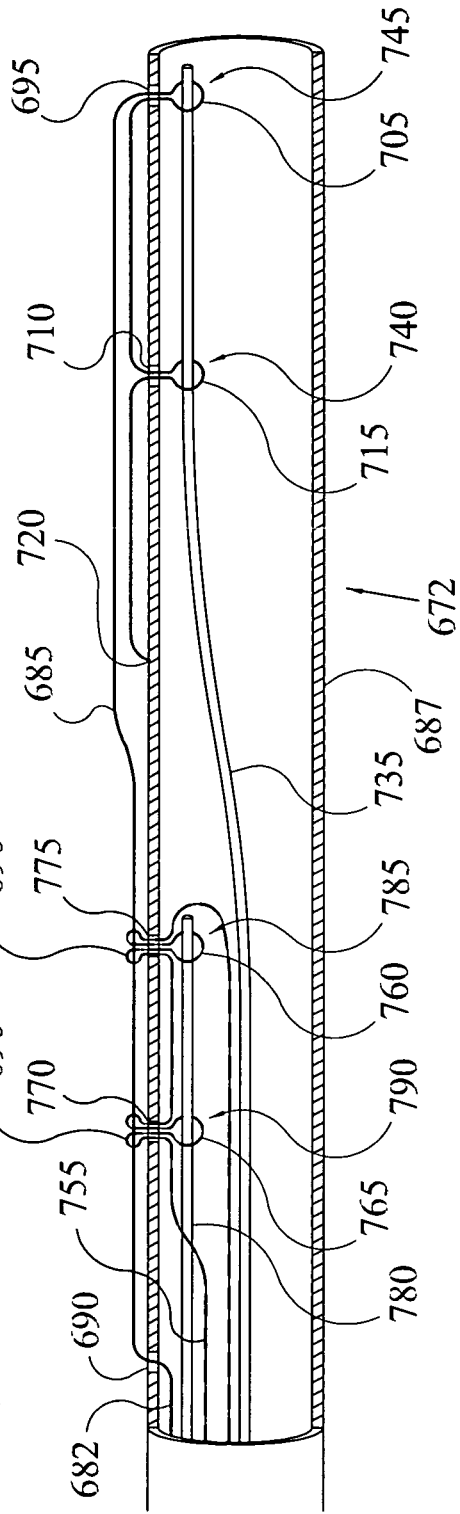

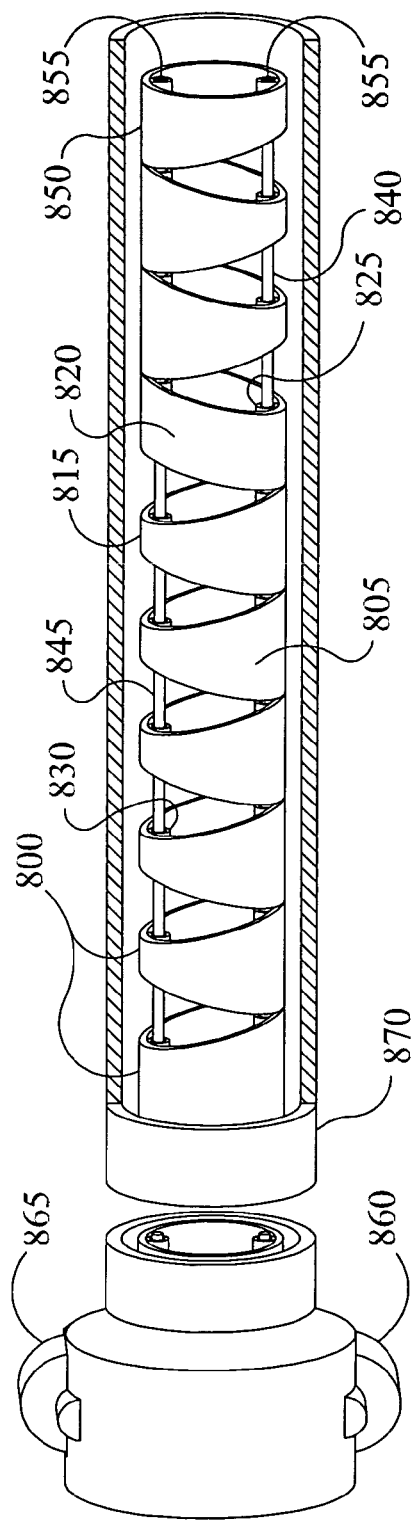
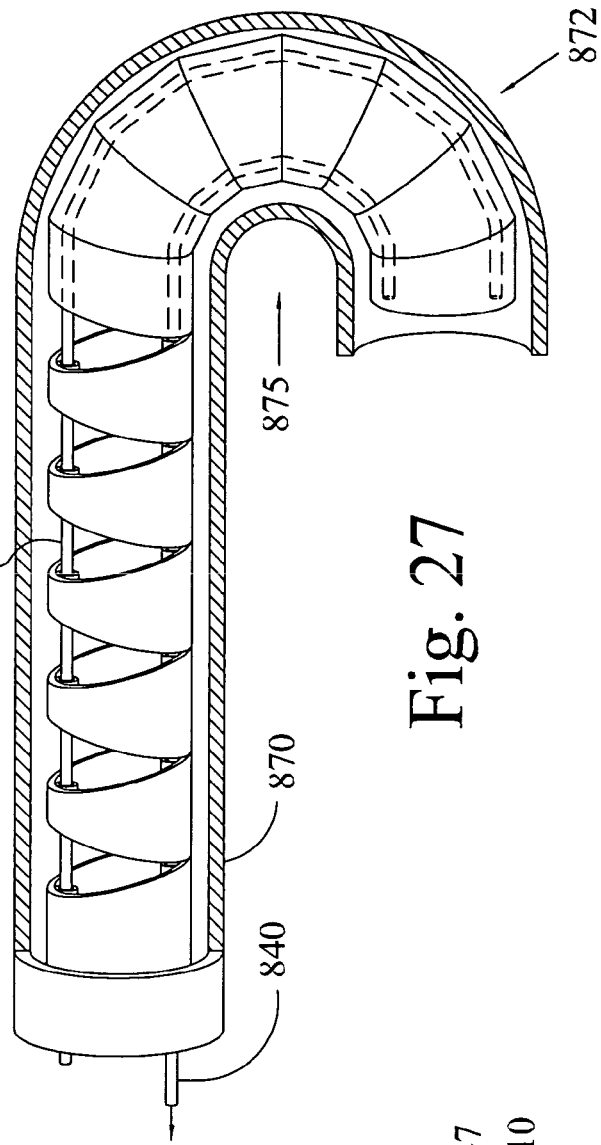
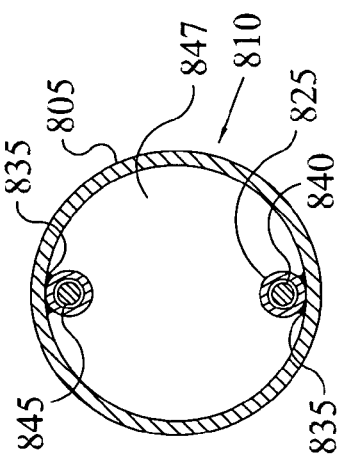
Fig. 26A
Fig. 26B
Fig. 27

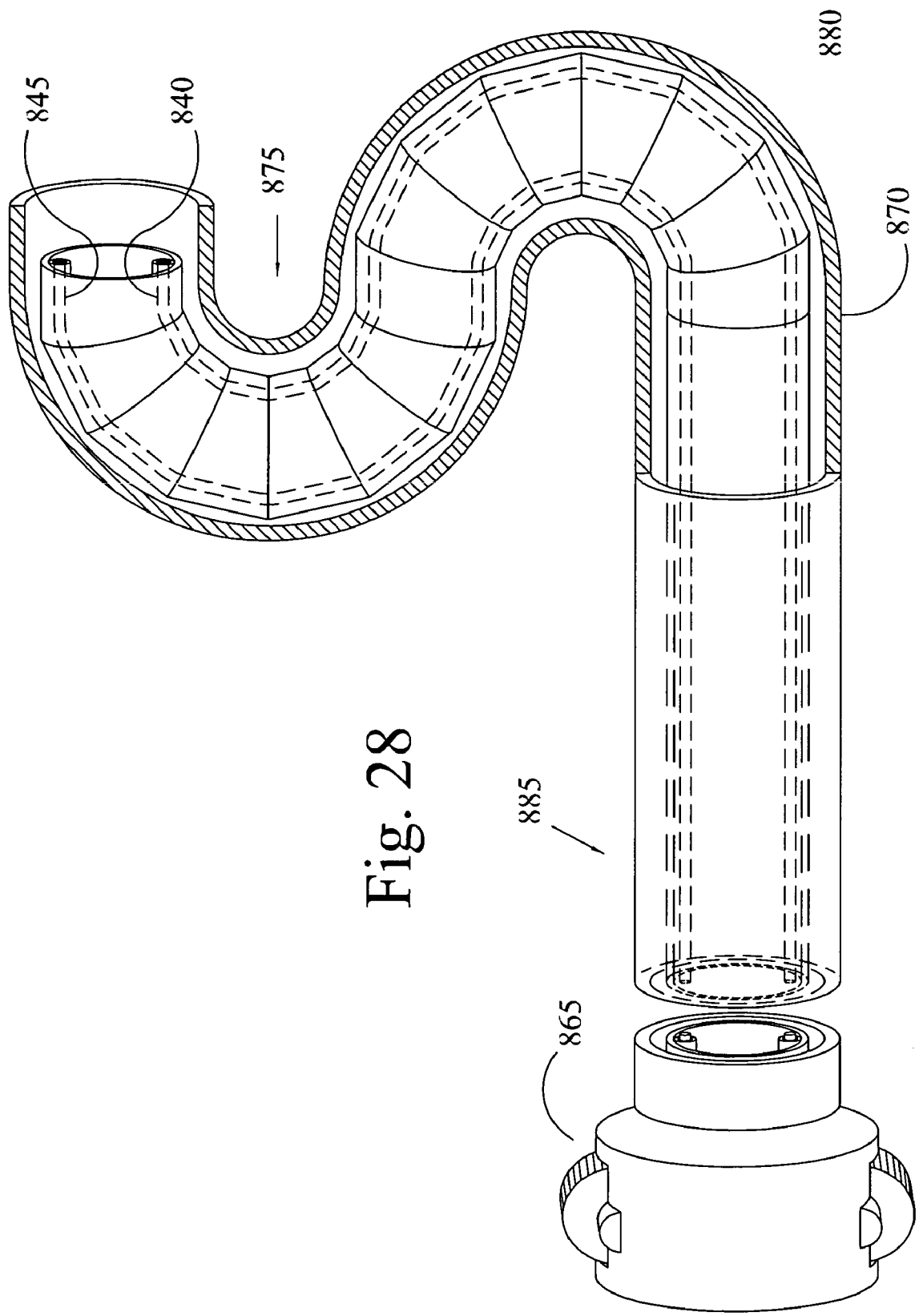

CLOSABLE LOOP ACCESS GUIDE CATHETER

CROSS REFERENCE TO RELATED APPLICATIONS

This application claims the benefit of provisional patent applications: 61/010,753 filed 11 Jan. 2008, 61/065,919 filed 15 Feb. 2008, 61/067,879 filed 3 Mar. 2008, 61/070,398 filed 21 Mar. 2008 and 61/190,088 filed 26 Aug. 2008 all by the inventor Joseph M. Thielen.

BACKGROUND OF THE INVENTION

1. Field of Invention

This invention relates to an interventional catheter that is placed within vessels of the body to provide access and support for another interventional catheter having passage within it and delivered to the site of a lesion.

2. Description of Prior Art

Access to coronary arteries, carotid arteries, and some peripheral vessels of the body for percutaneous therapeutic and diagnostic catheters is often made via guide catheters that are placed through introducer sheaths which are positioned into vessels that are most easily accessed from outside of the body. Such access sites include the common femoral artery, the brachial artery, and the radial artery.

Positioning of the guiding catheter into the ostium of the vessel to be treated can often be difficult, especially in diseased vasculature or in vessels that require the catheter to undergo a significant turn in the direction of travel. An additional problem that often occurs when trying to advance the percutaneous catheters through the guide catheter is that the guide catheter does not provide enough support for delivery of the percutaneous catheter and can result in the guide catheter backing out from the ostium of the vessel leading to the lesion to be treated. This problem can be exacerbated if the interventional catheter is stiff or carries a stiff element such as a stent thereby requiring a larger radius of curvature in the guide catheter to allow delivery of the interventional catheter or device.

Carotid artery interventional therapy has typically been performed via a percutaneous femoral access with delivery of a guide catheter or sheath through the aorta to the ostium of the brachiocephalic artery or the left common carotid artery. In diseased aortas the access to these ostii can be difficult and the support provided by this access can be inadequate to allow advancement of the therapeutic catheter.

The access catheter of the present invention can be used to provide access for carotid artery intervention via a radial or brachial artery approach. It can also be used to provide access to vertebral arteries or cerebral arteries or for other vessels that require good support from the guide catheter that cannot be obtained via standard guide catheters. The access catheter can also be used in the femoral artery or iliac artery in order to provide for support in going over the aortic arch. Additionally the access catheter can be used in venous vessels of the body and in other tubular members of the body that are being treated via interventional or minimally invasive techniques and undergo a significant turn in the tubular member.

On the right side of the body the radial artery or other arteries of the right arm lead proximally to the right subclavian artery which combines with the right common carotid artery to form the brachiocephalic artery that joins to the aorta. Access via the right radial artery with an access guide catheter would allow easy and direct access to the common carotid artery to perform an angiogram or to deliver interventional devices that are able to negotiate a small radius of curvature. Interventional catheters that are stiff and cannot undergo a tight turn such as a stent delivery catheter system cannot be easily delivered directly via the subclavian artery to the right common carotid artery.

If one continues to follow the vasculature proximally down the common carotid artery and through the brachiocephalic artery and into the aorta there currently is not a good option available to turn back and reenter the brachiocephalic artery with a guide catheter, and one would not obtain the necessary support in order to allow passage of a stiffer interventional catheter such as a stent delivery system within such a curved reentering guide without backing out the guide catheter. An access guide catheter intended for radial access also must be of a small profile in order to properly traverse the relatively small radial arteries of the arm.

On the left side of the body the radial artery or other arteries of the left arm lead proximally to the left subclavian artery which joins to the aorta. Currently there is not a good device option available to negotiate the small radius of curvature turn with a guide catheter and direct an interventional catheter distally down the left common carotid artery which is adjacent to the left subclavian artery along the aorta. The current curved guide catheters would not provide the support necessary to allow a relatively stiff interventional catheter such as a stent system to extend distally down the left common carotid artery without backing out of the ostium and yet have the low profile necessary to traverse the radial artery.

Carotid artery and other interventional therapy have typically been performed via a percutaneous femoral access with delivery of a guide catheter or sheath. The femoral artery is reasonably large in diameter and placing an introducer and guide catheter here for standard coronary angioplasty and stent procedures is very common. However for delivering larger interventional devices from this site can require guide catheters and sheaths that are relatively large and can cause blood flow blockage. Similarly, delivery of an introducer and guide catheter via the radial artery can cause radial artery blockage if the therapeutic catheter is similar in size to the blood vessel that it enters.

Interventional catheters having a larger distal aspect are often delivered within a relatively small artery causing blockage of blood flow in the small artery. This is often the case for carotid stent delivery systems where the distal aspect of the therapeutic catheter is significantly larger than the proximal shaft. The radial artery is large enough to accommodate the smaller proximal shaft diameter however the distal aspect can be too large to safely fit within the radial artery.

What is needed is a guide catheter that does not block blood flow proximally in the smaller radial artery, but provides guidance of the larger distal aspect of the therapeutic catheter in the larger carotid artery that can accommodate the larger diameter guide catheter and distal therapeutic catheter.

SUMMARY OF THE INVENTION

The access catheter of the present invention is an access guide catheter intended to provide access for a relatively stiff interventional catheter system such as a stent delivery system to the right or left internal, external, or common carotid artery via a radial artery approach. The access catheter can also deliver interventional devices to other vessels of the head and brain or to the peripheral vasculature of the body. The device can be used in arteries, veins, or other nonvascular tubular members of the body that have a significant directional change and require good support to advance an interventional device. The invention can also provide access across the iliac bifurcation from a femoral artery access. Furthermore, the invention describes a method for treating the carotid arteries that allows early delivery of a flexible temporary filter or filterwire to a site distal to the carotid lesion through the access guide catheter or a diagnostic sheath.

The access catheter is placed over a sheath, a guidewire, or both that extend on the left side of the body from the left radial artery to the left subclavian artery into the aorta where it forms a loop and then extends distally to the left common carotid artery. On the right side of the body the access catheter extends proximally from the right radial artery to the brachiocephalic artery into the aorta, forms a loop, and then extends distally back into the brachiocephalic artery. The loop that is located in the aorta is held in a closed conformation by a cord that provides the loop with a radius of curvature that can be smaller than would normally be required by a standard unsupported catheter and yet is large enough to allow passage of a relatively stiff interventional system. The closed loop conformation also allows the operator to tension the catheter in a proximal direction to provide the necessary support to allow delivery of the interventional catheter into the brachiocephalic or carotid artery on the right or left side respectively.

In one embodiment for the method of use on the right side of the body a shaped or steerable sheath can be advanced proximally over a wire to the junction of the subclavian artery and the common carotid artery. The sheath is then placed into the common carotid artery where an angiogram can be made and placement of a temporary filter wire can occur to protect the internal carotid artery from embolization of debris. The temporary filter wire (or standard guidewire if used) can be made to evert upon itself as it is advanced as a loop proximally down the brachiocephalic artery and into the aorta. The access guide catheter of the present invention is then advanced over the wire down the brachiocephalic artery into the aorta and then back into the brachiocephalic artery in a direction opposing the direction from which it originated.

A fiber that extends through the access catheter is then tensioned to cause the distal region of the access catheter to form a closed loop located within the aorta. The closed loop in the access catheter then provides a larger radius of curvature bend than would be possible if formed in the brachiocephalic artery for which the interventional catheter such as a stent system can easily follow. Support is provided by the access catheter by placing tension on the access catheter to counteract the pushing force applied to the interventional catheter. The interventional catheter can then be advanced through the access catheter and over a guidewire to the internal carotid artery to perform a carotid therapy such as carotid stent placement.

The method of use on the left side of the body employs a similar procedure to deliver the access guide catheter from the left subclavian artery to the left common carotid artery. The access catheter of the present invention is advanced over a sheath or guidewire from the left radial artery through the left subclavian artery into the left common carotid artery forming a loop in the aorta. A loop is formed in the access guide catheter via tensioning of a fiber and the loop is held tight to form a closed loop due to a filament that is attached near its distal end. Following removal of the sheath the access catheter is available for delivery of the interventional catheter such as a carotid stent system.

As an alternate embodiment, the access guide catheter can be a shaped catheter having a bend or curve in it that holds a hooked shape. The bend is straightened during delivery via a stiffening element. Once the guide catheter is in position, the stiffening element is withdrawn and the bend is reformed. An interventional catheter is able to follow within this curved portion of the guide catheter and is redirected at an appropriate angle of travel.

A further embodiment to the access guide catheter having a closed loop is intended primarily for delivering the guide catheter down one vessel and directing it back in an opposing direction using two different fibers. This guide catheter has a flexible distal region that is steered by a steering fiber to direct the distal region into a loop. The catheter also has a second cinch fiber that forms a loop in the less flexible, loop region of the catheter. This embodiment provides a closed loop for delivery of a catheter from one vessel and back 180 degrees in an opposing direction down the vessel from which it came. The loop region provides support for an interventional catheter to pass from the radial artery down into the loop formed in the aorta and back up the brachiocephalic artery to provide access to the carotid artery for treatment. This embodiment allows the guide catheter to be placed from an artery and back into that same artery without the need or stiffening mandrels or to follow a guidewire to form the loop.

The radial artery is small in diameter ranging from 2-5 mm in diameter. Often the stent delivery systems used to deliver a 6-8 mm carotid stent are 6 French or larger in profile. If one were to use a standard 7 French guide catheter to deliver a 6 French stent delivery system, the shaft of the guide catheter would be too large for the radial artery but this diameter is very acceptable for the significantly larger carotid artery where the vessel lesion is located. The stent delivery system, however, only requires a large profile in the distal aspect of the delivery system where the stent resides; the proximal shaft of the stent delivery catheter can be significantly smaller and fit well within the diameter of a radial artery without causing vessel blockage or thrombosis.

One embodiment of the present system overcomes this problem by providing a guide catheter that has a rapid exchange design. The distal guide segment or portion of the guide catheter is large enough to provide access for the large distal aspect of the therapeutic catheter and allows the smaller shaft region of the therapeutic catheter to reside along side the smaller proximal element of the guide catheter. The smaller proximal element connects the distal guide segment located within the vessel with the manifold located outside the body. The distal guide segment can have one or two fibers that are integrated with the catheter to help steer the distal portion to form a curve or loop to provide support and direct an interventional catheter in an opposing direction.

Another embodiment of the rapid exchange guide catheter allows the distal guide region to undergo a passive expansion once it is delivered into the blood vessel through the introducer. The distal guide region can be formed with a braided or expandable structure that has its equilibrium dimension as its expanded diameter. This diameter can be reduced during delivery through the introducer.

In an additional embodiment the access guide is provided entry into a blood vessel over a segmented mandrel that can transform from a floppy mandrel to one that has a specific shape and is rigid. The segmented mandrel is entered into the aorta in a flexible condition. The segmented mandrel is then tensioned to cause it to form a curved shape that is stiff. The access guide catheter is then advanced over the stiffened and curved segmented mandrel to provide access to a vessel that is at a sharp angle from the vessel of origin. The segmented mandrel is then allowed to relax and is removed from the vessel leaving the access guide in place.

In an alternate embodiment for the access catheter, the distal region that forms the loop has a steering fiber that initiates the curve in the distal end of the guide catheter. The catheter also has a cinch fiber that pulls the distal region into a closed loop. A multiplicity of temporary attachment sites allows the distal end of the catheter to be deployed into a loop within the aorta without making contact with the aortic wall. A plurality of openings for the attachment fiber along with a plurality of temporary attachment sites for the fiber allows the catheter to be advanced distally within the vessel that requires access.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1A is a sectional view of the access guide catheter.

FIG. 1B is a plan view of the access guide catheter having a closed loop.

FIGS. 5A-5B are plan views of a steerable sheath in a straight and curved configuration.

FIGS. 6A-6C are views of the access guide catheter delivered to the right common carotid artery from the right subclavian artery.

FIGS. 7A-7C are views of the access guide catheter delivered to left common carotid artery from the left subclavian artery.

FIG. 8 is a plan view of a shaped guide catheter.

FIG. 9 is a partially sectioned view of a shaped guide catheter with a sheath and stiffening mandrel therein.

FIG. 10A shows a sectioned view of a sheath.

FIGS. 10B and 10C show partially sectioned views of the distal region of an access guide catheter having a sheath, mandrel, and guidewire therein in a straight and curved conformation.

FIG. 11B shows a partially sectioned view of an access guide catheter being steered into a closed loop.

FIG. 11C shows a partially sectioned view of an access guide catheter being cinched into a closed loop.

FIG. 13 is a sectional view an access guide catheter positioned over a tapered sheath.

FIG. 14 is a partially sectioned view of the distal portion of an embodiment of an access guide catheter.

FIG. 15 is a partially sectioned view of an access catheter of FIG. 14 located in the aorta and left subclavian artery.

FIGS. 16A-C are views of the access guide catheter extending from the left subclavian artery to the left common carotid artery.

FIGS. 23A-E are views of an access guide catheter having releasable attachment points positioned a sheath and located in one of the great vessels extending into the aorta and back into the great vessel from which it forming a closed loop.

FIG. 24A is a partially sectioned view of an embodiment of an access guide catheter having releasable fiber openings and releasable attachment points.

FIG. 24B is a partially sectioned view of an embodiment of an access guide catheter having releasable fiber openings and releasable attachment points.

FIG. 26A is a partially sectioned views of a segmented mandrel positioned within an external catheter such as an access guide catheter.

FIG. 26B is a cross-sectional view through one segment of the segmented mandrel.

FIG. 27 is a partially sectioned view of the segmented mandrel positioned within an external catheter and forming a curved shape.

FIG. 28 is a partially sectioned view of the segmented mandrel positioned within an external catheter and forming two curves.

DETAILED DESCRIPTION OF THE INVENTION

Figure 1C:
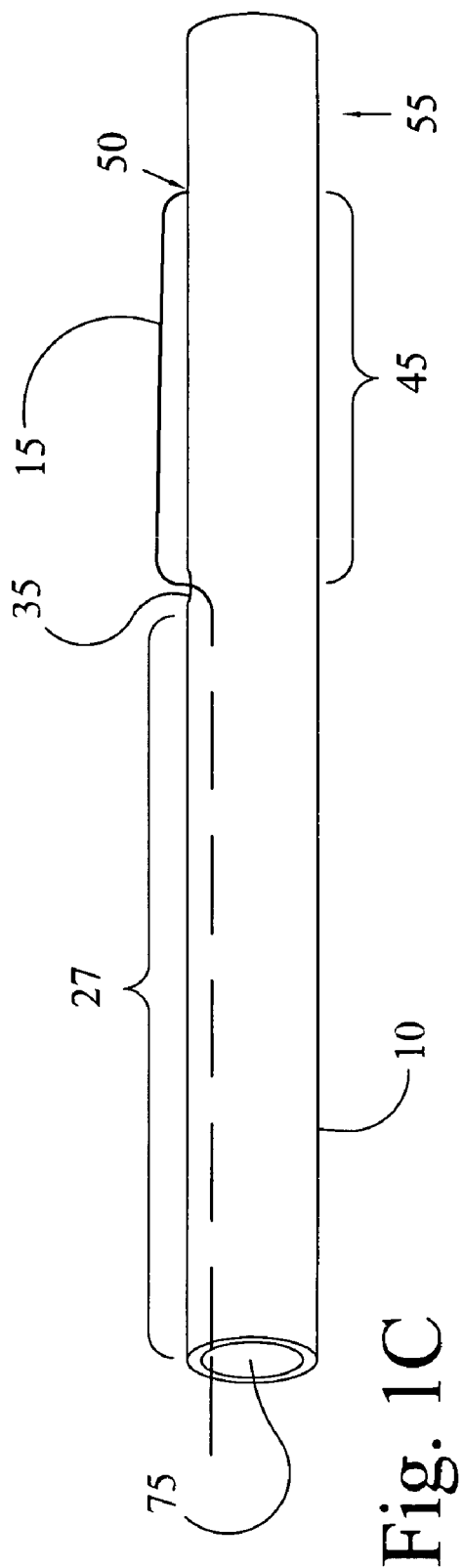
FIG. 1C is a plan view of the distal region of one embodiment of the access guide catheter.

The present invention is an access guide catheter that is low profile to allow access via a radial artery approach and provides support for passage of an interventional catheter such as a stent system by forming a closed loop conformation. Larger catheters can also be formed using the present invention for other tubular vessels and applications not limited by vessel size. The low profile is accomplished by providing a very thin fiber that attaches near the distal region of the catheter and forces it to form a closed loop in the loop region of the catheter but still provide a great deal of support even though the wall thickness is thin and flexible. Support is provided by the closed loop which does not open up or back out of an ostium as tension is applied to the access guide catheter and an interventional catheter is being advanced within it.

FIG. 1A shows one embodiment of the access guide catheter (5) of the present invention. It is a 5-6 F catheter intended to fit well within the radial artery or other vessels of the body. As shown in this embodiment, the catheter shaft (10) can be a dual lumen extrusion of a polymer such as polyethylene, pebax, polyurethane or other polymer commonly used in the medical catheter devices. A fiber (15) extends from the proximal end (20) of the access guide catheter (5) and is contained in the fiber lumen (25) of the contained region (27) located in the proximal region (30) of the access guide catheter (5) and exits a small opening or fiber opening (35) in the wall (37) of the catheter (5) at the proximal end (40) of the looped region (45). The fiber (15) further extends distally on the outside of the access guide catheter (5) in the loop region (45) and is attached at an attachment point (50) located proximal to the distal region (55) and distal end (57) of the access guide catheter (5). The distal region of the access guide catheter (5) is intended to extend into the vessel to which access is intended for delivery of an interventional catheter. The fiber (15) is able to move within the fiber lumen (25) and move with respect to the fiber opening (35). The fiber (15) is attached at the proximal end (20) of the access guide catheter (5) to a locking element (60) that is located on the manifold (65) of the device. The tensioning element (70) is activated to create tension in the fiber (15), as the catheter shaft (10) forms a loop in the loop region (45). As shown in FIG. 1B, the attachment point (50) is brought into contact or near contact with the opening (35). The locking element (60) is used to hold the fiber (15) and hold the loop into a closed loop conformation. The diameter of the loop is smaller than 2.5 cm to allow the loop to fit within a typical aorta for providing access to carotid arteries or vessels of the head. The loop provides a relatively large radius of curvature, typically providing a diameter of approximately 2.5 cm to allow easy passage of a therapeutic catheter such as a stent delivery system through the access lumen (75).

FIG. 1C shows and alternate embodiment of the access guide catheter (5) where the catheter shaft (10) is formed of a single tubular structure and the fiber (15) is contained within the access lumen (75) that provides passage also for other interventional catheters. The fiber (15) again extends out of a small opening (35) in the wall of the catheter shaft (10) and is attached at an attachment point (50). In this embodiment, the contained region (27) of the catheter shaft (10) is formed of a stiffer polymer than the loop region (45) to preferentially cause the loop region (45) to form a loop when the fiber (15) is placed into tension while maintaining the contained region (27) less prone to bending. The distal region (55) extends distally from the attachment point (50).

Figure 1D:
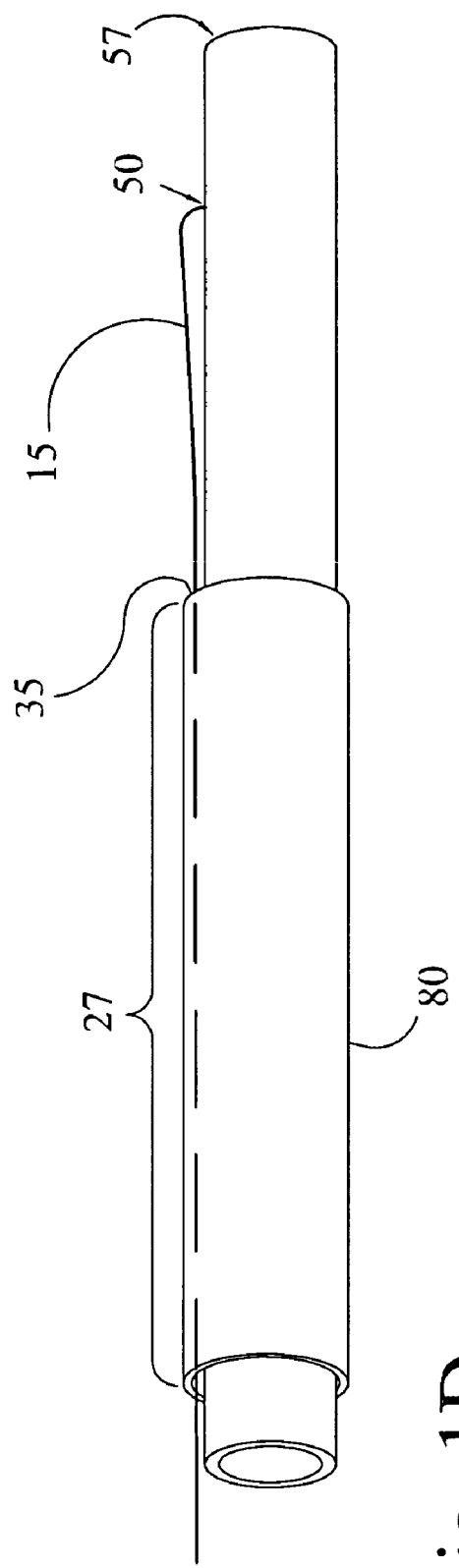
FIG. 1D is a plan view of the distal region an embodiment of the access guide catheter.

FIG. 1D is another embodiment having an external sheath (80) located in the contained region (27) of the access guide catheter (5). The external sheath (80) can be a thin wall polymeric covering, a metal or polymeric coil, a series of rings, or other member that provides a pathway for fiber movement in the contained region (27) of the access guide catheter (5). A small tube attached to the outside of the catheter shaft (10) can also provide housing for the fiber (15). The fiber opening (35) can be the distal end of the sheath (80). It is noted that the distal flexible portion of the present access guide catheter (5) can be shortened or truncated. The attachment point (50) can be located very near or adjacent to the distal end (57) of the access guide catheter (5).

Figure 2:
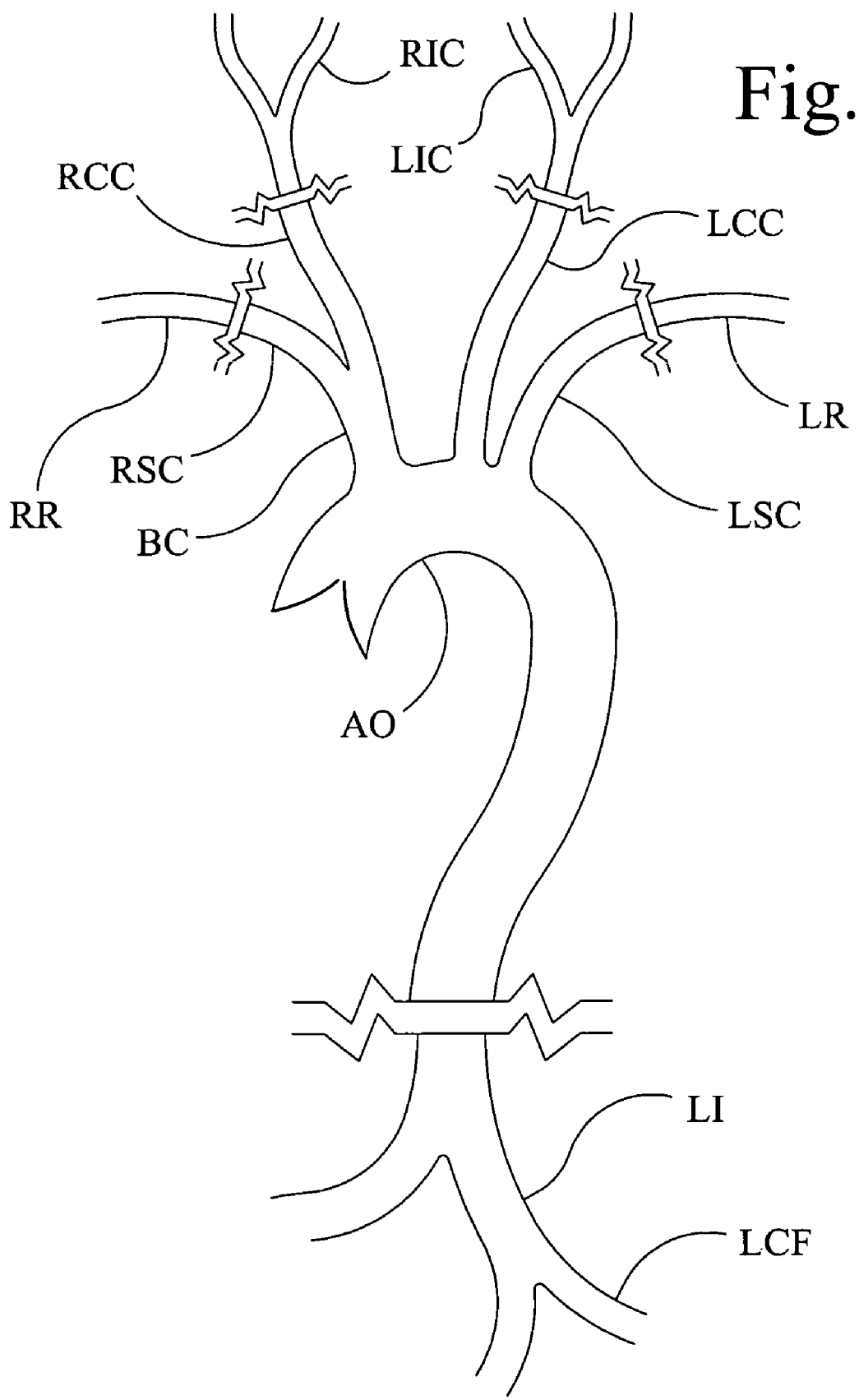
FIG. 2 is a sectional view of the aorta and great vessels.

The location of the brachiocephalic artery (BC), the left common carotid artery (LCC), and the left subclavian artery (LSC) with respect to the aorta (AO) is shown in FIG. 2. During percutaneous procedures that are intended for therapy of the left internal carotid artery (LIC) or the right internal carotid artery (RIC) with access from the left common femoral artery (LCF), it is difficult for the operator to provide good support for the guide catheter into the Great Vessels because the aortic wall on the opposite side does not provide consistent or adequate support due to its geometry. Access to these vessels and support is even worse for diseased aortas that are distorted and calcified. The present access guide catheter is intended to overcome these problems of BC and LCC vessel access and guide catheter support, and also provide a low profile system that can enter percutaneously into the left radial artery (LR) or right radial artery (RR). As shown in FIG. 2, the right radial artery (RR) extends proximally to the right subclavian artery (RSC) which then intersects with the right common carotid artery (RCC). Although the turn from the right subclavian artery (RSC) to the right common carotid artery (RCC) is tight, flexible devices with low radius of curvature may be able to access directly through this tight turn. Additionally, it is the intent of the access guide catheter of the present invention to be able to direct a catheter from the right radial artery (RR) through the right subclavian artery (RSC) and down the brachiocephalic artery (BC) into the aorta (AO); here the access guide catheter forms a closed loop and extends distally back up the brachiocephalic (BC) and finally provides a passage for a device that can extend into the right internal carotid artery (RIC). On the left side, the access guide catheter extends from the left radial artery (LR) through the left subclavian artery (LSC) and into the aorta (AO) where it forms a closed loop and extends distally down the left common carotid artery (LCC) for delivery of a therapeutic device such as a stent to the left internal carotid artery (LIC). The present invention can be used in other vessel anatomy also which requires a significant turn in the direction of travel.

Figure 3A:
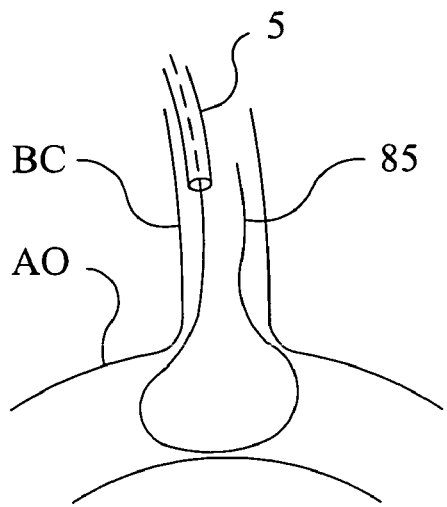
FIGS. 3A-3D are views of the access guide catheter delivered to the brachiocephalic artery.
Figure 3B:
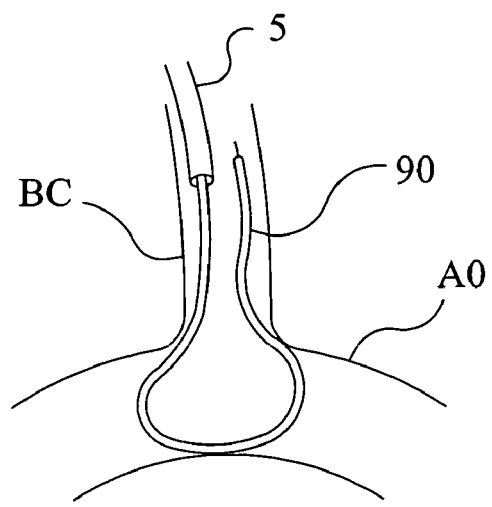
Figure 3C:
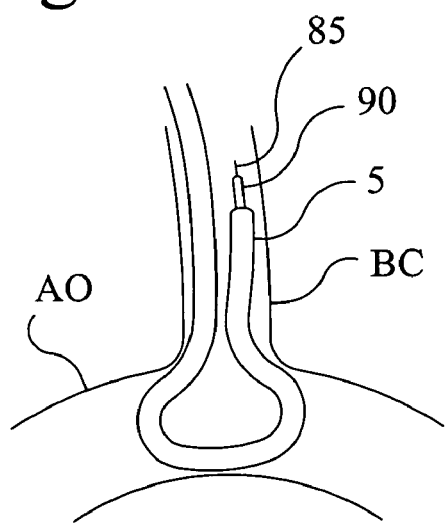

The general use of the access guide catheter (5) is shown for the right side of the body in FIGS. 3A-3D. In FIG. 3A a guidewire (85) is shown looped into a large vessel such as the aorta (AO) from another side vessel such as the brachiocephalic artery (BC). The guidewire (85) can be of a diameter ranging from 0.014 to 0.035. It can be a portion of a 0.014 filter-guidewire that extends distally to a filter portion that is located distal to a lesion in the right internal carotid artery (RIC). The other end of the guide wire (85) could extend percutaneously from the patients radial artery. A commonly used sheath (90) can be placed over the guidewire (85) and following the loop located in the aorta (AO) as shown in FIG. 3B. The sheath (90) can be a 3-4 Fr. sheath that allows passage of the access guide catheter (5) over it and helps direct the access guide catheter (5) into a loop. FIG. 3C shows the access guide catheter (5) of the present invention following over the combination of sheath (90) and guidewire (85) as it forms a loop in the aorta (AO).

Figure 3D:
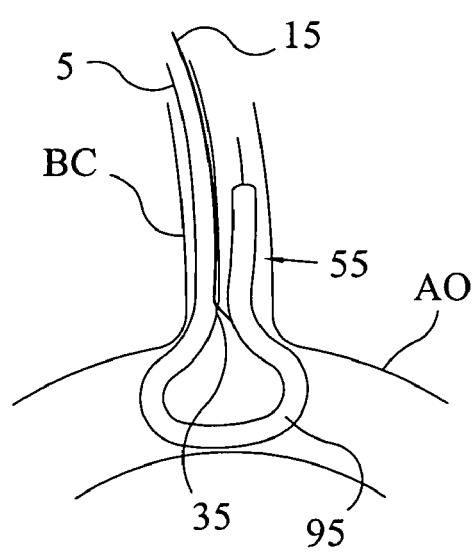

Finally, FIG. 3D shows the access guide catheter (5) forming a closed loop (95) in the aorta (AO) as the fiber (15) pulls the attachment point (50) into contact with the fiber opening (35). With the sheath (90) removed, the access guide catheter is ready to provide passage for an interventional catheter such as a stent system. The stent system can be delivered over the 0.014 guidewire (85) and within the access guide catheter (5). Providing tension to the access guide catheter (5) by pulling on the proximal end of the access guide catheter (5) that extends percutaneously from the patient provides support for the interventional catheter such that the distal region (55) of the access guide catheter (5) will not back out of the ostium of the brachiocephalic artery (BC).

Figure 4A:
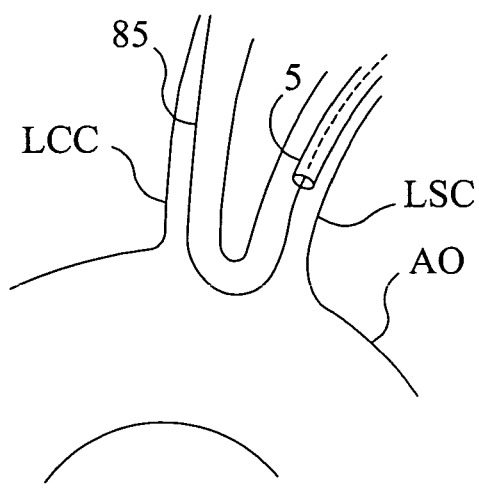
FIGS. 4A-4D are views of the access guide catheter delivered to the left common carotid artery.
Figure 4B:
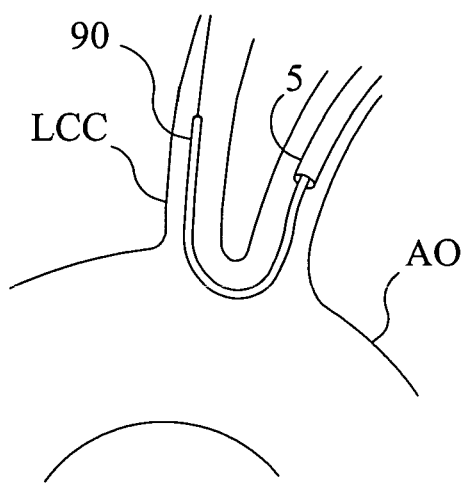
Figure 4C:
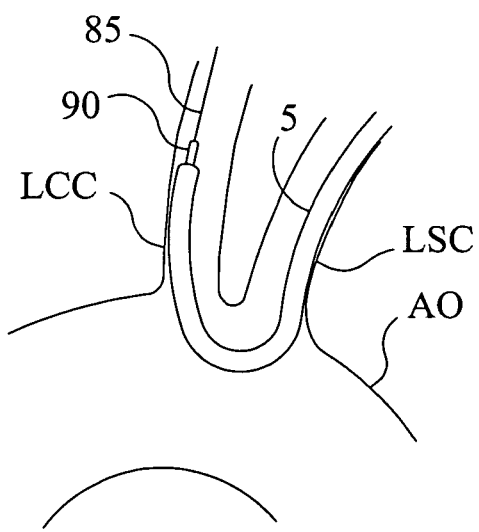
Figure 4D:
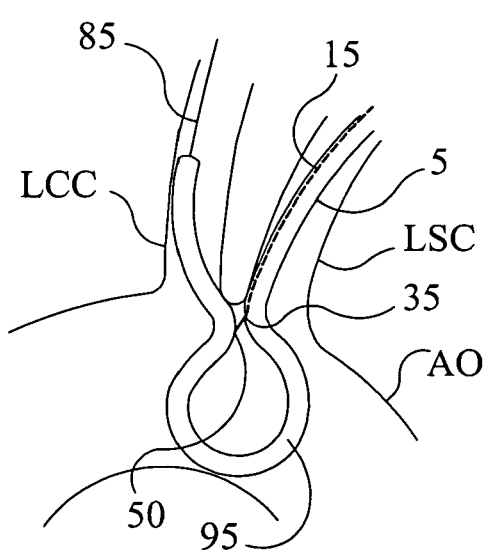

The general use of the access guide catheter (5) for the left side of the body is shown in FIGS. 4A-4D. FIG. 4A shows a guidewire (85) of diameter ranging from 0.014-0.035 inches extending from the left subclavian artery (LSC) to the left common carotid artery (LCC). The guidewire (85) can extend further up the left common carotid (LCC) to the left internal carotid (LIC) and be an attached component of a filterwire placed distal to a carotid lesion that is to be treated. The other end of the guidewire (85) can extend down the left subclavian (LSC) to the left radial artery (LR) and extend percutaneously outside of the body. A sheath (90) is shown in FIG. 4B extending from the left subclavian artery (LSC) to the left common carotid artery (LCC). The sheath (90) can be a 3-4 Fr sheath and it can contain a guidewire within a lumen. FIG. 4C shows the access guide catheter (5) following over the sheath (90) as it extends from the left subclavian artery (LSC), forms a loop in the aorta (AO), and extends distally into the left common carotid artery (LCC). FIG. 4D shows the access guide catheter (5) with the fiber (15) under tension pulling the attachment point (50) into contact with the fiber opening (35) and forming a closed or solid loop (95). The sheath has been removed to provide for passage for an interventional catheter that would be placed via the left radial artery (LR) though the access guide catheter (5) and into the left common carotid artery (LCC). The interventional catheter could be advanced along a guidewire if necessary to the internal carotid artery for treatment of a vascular lesion. The support provided by the access guide catheter (5) is due to tension being placed on the access guide catheter (5) and transmission of this support to the closed loop (95) located in the aorta (AO), by way of the left subclavian artery (LSC), and left common carotid artery (LCC).

The method of use for treating the carotid artery via a radial approach provides significant advantages over the femoral approach. The radial approach obviates the access difficulty to the great vessel from a diseased aorta that is found with a femoral approach and can potentially provide for better support by using the access guide catheter (5) of the present invention with a closed loop (95). In addition, it may be possible to place a distal embolization filter easier and earlier in the procedure via a radial approach thereby reducing the risk for embolization of debris to the brain and subsequent complications due to stroke. A radial approach will also overcome many of the groin access closure complication and length of stay for the patient and as a result have a definite impact on the cost of the procedure. The method for providing diagnostic angiography, placement of an embolization filter, delivery of the access guide catheter, and delivery of the therapeutic catheter such as a stent delivery catheter via a radial approach are described in the following figures. A method will be described for gaining access to the right and left internal carotid arteries via the right and left radial arteries. Two different sheaths will be described to help gain access to the carotid arteries. One is a steerable catheter that allows its distal region to change from being flexible to having a hook shape; the other is a shaped sheath that has a built-in hook shape. The shaped catheter often can have a thermally shaped hook shape with appropriate stiffness as controlled by the wall thickness and type of polymer used to form the hook region. The shaped catheter can be used with a shaped guidewire as described further to facilitate the support that the sheath transmits to the access sheath where the access guide catheter is being placed.

FIG. 5A shows a steerable sheath (100) that has a stiff region (105) and a flexible region (110). A tensioning cord (115) runs through the cord lumen (120) of the catheter body (125). The cord (115) attaches to the distal end of the catheter body (125) at the cord attachment (130). A tensioning element (135) located on the manifold (140) provides tension in the proximal direction (145) shown in FIG. 5B to the tensioning cord (115) which moves within the cord lumen (120) and causes the flexible region (110) to form a "J" shape or hook shape (150). This hook region or curved region (155) can provide the support for passage of a flexible device such as some of the embolic protection filter wires through a radius of curvature of approximately 0.2-0.4 inches. Also the steerable sheath (100) can be used to provide for diagnostic angiography through the access lumen (160). Additionally, the steerable sheath (100) can be of a 3-4 Fr diameter and can provide passage for a preloaded guide catheter over its exterior surface. The tension lock (165) FIG. 5A can be engaged to hold the hook shape (150) when the tensioning cord (115) is under tension; the tension lock (165) can be deactivated allowing the hook shape (150) to be released and the flexible region (110) to once again be flexible. This steerable sheath (100) can also be formed into a shaped sheath with a hook similar to that shown in FIG. 5B through thermal forming of the polymer shaft.

The method of use for access to the right side of the body using a 3-4 Fr. steerable sheath (described in FIGS. 5A and 5B) is shown in FIGS. 6A-6C. An 0.018, 0.025, or 0.035 guidewire (not shown) is placed into an introducer catheter located in the right radial artery (RR) and advanced through the right subclavian artery (RSC) to the brachiocephalic artery (BC) and into the aorta (AO). The steerable catheter or sheath (100) is advanced over the wire to the right common carotid artery (RCC). The wire is retracted and the steerable sheath (100) is steered by tightening the tensioning cord (115) and directing the hook (150 add to FIG. 6A) into the right common carotid artery (RCC) as shown in FIG. 6A. An angiogram is taken and a filter wire (205) can be advanced directly into the right common carotid artery (RCC) and the filter (210) is further advanced to the right internal carotid artery (RIC) to a site distal to the lesion (215) to be treated. Alternately, a guidewire can be advanced into the right internal carotid artery (RIC). The steerable sheath (100) is then retracted slightly from the right common carotid artery (RCC) and the tension cord (115) is released. The wire portion of the filter wire (205) is everted down the brachiocephalic artery (BC) and forms a loop (220) in the aorta (AO) as shown in FIG. 6B. The steerable sheath (100) is then advanced over the everted guidewire (205) following it along the brachiocephalic artery (BC) into the aorta (AO), around the loop (220), and back into the brachiocephalic artery (BC). The access guide catheter (5) is then advanced over the combination of guidewire (205) and steerable sheath (100) forming a loop (95) in the aorta (AO) and extending into the brachiocephalic artery (BC). An additional guidewire may be placed within the steerable sheath (100) to provide additional support for the access guide catheter (5). The fiber (15) is then tensioned in the access guide catheter (5) pulling the attachment point (50) into contact with the fiber opening (35) in the access guide catheter (5) and forming a closed loop (95) in the aorta (AO) as shown in FIG. 6C. The steerable sheath (100) is then removed allowing for passage of an interventional catheter within the access guide catheter (5) and over the wire portion of the filterwire (205) for advancement into the right internal carotid artery (RIC).

The method of use for access to the left side of the body using the steerable sheath (100) is shown in FIGS. 7A-7C. A guidewire (200) is advanced via the left radial artery through the left subclavian artery (LSC) and into the aorta (AO). The steerable sheath (100) is advanced over the guide wire (200) into the aorta (AO). The guide wire (200) is retracted and the steerable sheath (100) is tensioned by placing tension on its tension cord to form a hook (150) which is directed into the left common carotid artery (LCC) as shown in FIG. 7A. An angiogram is taken and a filter wire (205) or standard guidewire is advance through the left common carotid artery (LCC) into the left internal carotid artery (LIC) distal to the site of the lesion (215) to be treated. The filter (210) would be placed distal to the lesion (215). The access guide catheter (5) is then advanced from the radial artery through the left subclavian artery (LSC) over the steerable sheath (100) into the left common carotid artery (LCC) as seen in FIG. 7B. An additional stiffening wire can be placed in the sheath (100) to help support the advancement of the access guide catheter (5) into the left common carotid artery (LCC). The fiber (15) of the access catheter (5) is tensioned to bring the attachment point (50) into contact or near contact with the fiber opening (35) and form a closed loop (95) in the aorta (AO) as shown in FIG. 7C. The steerable sheath (100) is then removed and the interventional catheter is advanced within the access guide catheter (5) and over the filterwire (205) to the lesion site. Tension is applied to the proximal end of the access catheter (5) to provide support of the closed loop (95) of the access guide catheter (5) and counteract the pushing force applied to the interventional catheter.

The method of use for access to the right side and left side of the body using a shaped sheath is similar to that described earlier for the steerable sheath. The use of a stiffening mandrel or guidewire to hold the steerable sheath in a linear manner during delivery and removal or repositioning of the wire or mandrel allows the distal end of the shaped sheath to form a hook shape. The shaped sheath can be a tubular sheath having a hook shape in its natural state. The hook shape allows other catheters to follow over it around a turn It is understood that the access guide catheter may be preloaded onto the steerable sheath or the shaped sheath such that the manifold that is associated with the sheath is on the outside of the manifold for the access guide catheter thereby allowing the sheath to be removed following placement of the access guide catheter in the carotid or brachiocephalic artery. It is understood that combinations of the guidewires and sheaths along with other stiffening catheters or wires can be used to enhance access and support.

An alternate embodiment of the present invention is a shaped guide catheter that is low profile to allow access via a radial artery approach and provides support for passage of an interventional catheter such as a stent system by forming a stiff curve. Support is provided by the stiff curve which does not open up or back out of an ostium as tension is applied to the shaped guide catheter and an interventional catheter is being advanced within it. The catheter is delivered from one vessel and makes a 180 degree turn and is delivered in an opposing direction to a vessel from which it came.

FIG. 8 shows one embodiment of the shaped guide catheter (235) of the present invention. It is a 6 F (ranges from 4 F to 8 F) catheter intended to fit well within the radial artery or other vessels of the body. As shown in this embodiment, the catheter shaft (240) can be a single lumen extrusion of a polymer commonly used in the medical catheter devices. A braid of metal or polymeric fiber can be placed in the curved region (245) and can extend into all or a portion of the shaped guide catheter (235) proximal to the curved region (245) to prevent kinking as well as to provide more rigidity or stiffness to the tubing for support. A marker line (250) that can be viewed on Fluoroscopy can be placed axially in the curved region (245) to help align the direction of the curved region (245). The distal region (255) of the shaped guide catheter (235) is intended to be flexible and track easily over a sheath or guidewire. The curved region (245) provides a relatively large radius of curvature, typically around 0.4 to 1.2 inches to allow easy passage of a therapeutic catheter such as a stent delivery system.

The shaped guide catheter (235) is intended for delivery within a vessel of the body in a generally straight condition where the curved region (245) is substantially straightened temporarily by a straightening element such as a mandrel, a sheath, a guidewire, or other element contained within its lumen. When the straightening element is removed, the shaped guide catheter (235) tends to form a 180 degree curve as shown in FIG. 8. The stiffer curved region (245) along with the stiff neck region (260) which extends proximally from the curved region (245) by approximately 5 cm (ranges from 1 cm to 20 cm) provides the support necessary for advancement of a therapeutic catheter within its lumen. The entire proximal region (265) can also be stiff in order to provide support.

The shaped guide catheter (235) of the present invention as shown in FIG. 9 can track over a sheath (270). The sheath is a polymeric tube having a lumen which is intended to provide passage for or contain a guidewire (275) and a stiffening mandrel (280). The sheath (270) can be a duel lumen tubing where one lumen is intended for a guidewire (275) and the other is intended for a stiffening mandrel (280). The sheath (270) can be a shaped sheath or it can be a steerable sheath similar to that described previously in FIG. 5.

The stiffening mandrel (280) is a metal rod or stiff material tube (282) that is more flexible in the distal region (285). The tubular stiffening mandrel (282) can provide passage for a guidewire (275) within it such as a 0.014 guidewire or the shaft of a filterwire. The flexible distal region (285) can be formed via thermal processing such as annealing or it can be formed by joining two tubes of differing rigidity together as well as machining a pattern of grooves into the wall of the tube.

FIG. 9 shows an assembly of the shaped guide catheter (235) containing a sheath (270) which contains a stiffening mandrel (280). If the stiffening mandrel (280) has a tubular conformation, a guidewire can pass through it. The curved region (245) of the shaped guide catheter (235) is held in a generally straightened conformation due to the presence of all the internal components including the sheath (270) and guidewire (275), but especially due to the presence of the stiffening mandrel (280). The shaped guide catheter (235) can be preloaded onto the sheath (270) prior to introduction into the vessel to allow the sheath (270) to be removed after the shaped guide catheter (235) is in place. The manifold (290) for the sheath (270) is located in this embodiment proximal to the manifold (295) for the shaped guide catheter (235). Removable manifolds and rapid exchange catheters and sheaths are also anticipated as possible alternatives for the devices and methods described in this invention.

Figure 10C:
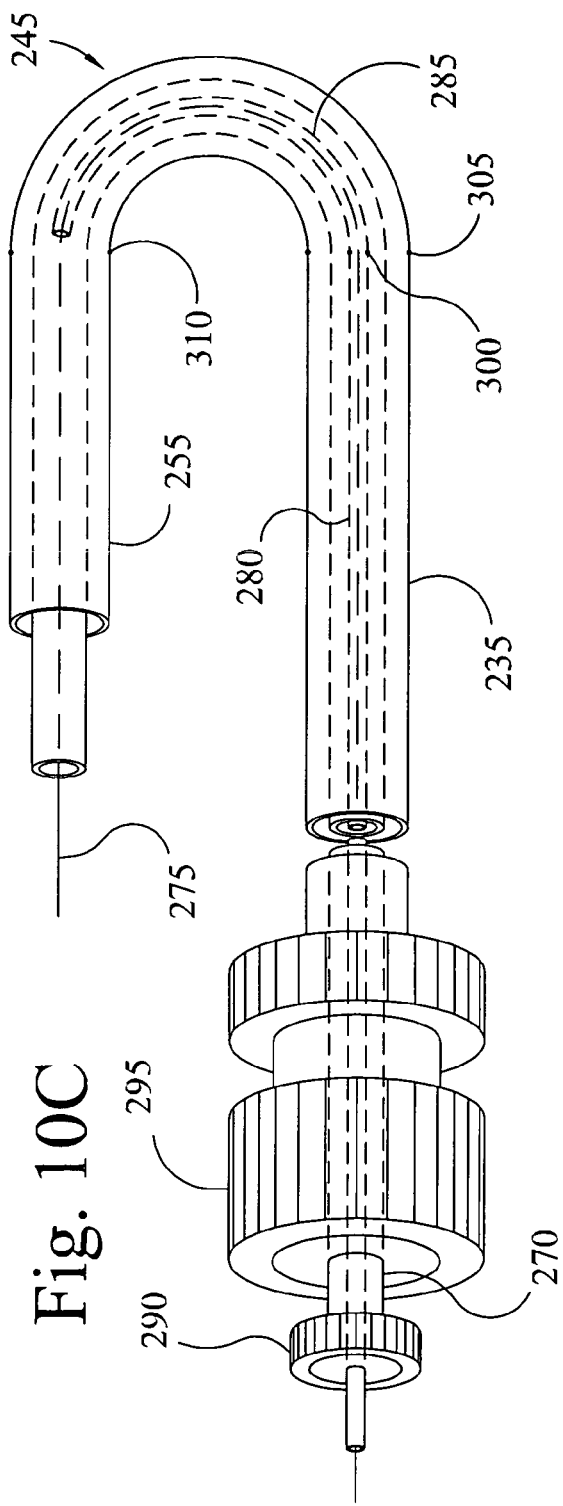

FIGS. 10A-10C shows the general steps involved with placing the shaped guide catheter (235) within a vessel. First it is assumed that a guidewire (275) and sheath (270) are positioned within the vessel of interest. A stiffening mandrel (280) such as the one shown in FIG. 10A is advanced over the guidewire (275) and within the sheath (270) such that the distal mandrel region (285) is contained within the sheath (270) and the junction (300) (shown by a dot) of the more flexible distal mandrel region (285) and the stiffer proximal mandrel region (287) of the stiffening mandrel (280) is located within the vessel at a position that is intended for the proximal end (305) of the curved region (245) of the shaped guide catheter (235). The shaped guide catheter (235) is then advanced over the sheath (270) such that the distal end (310) of the shaped or curved region (245) (shown by a dot) is at the same position as the junction (300) of the stiffening mandrel (280). Upon further advancement of the shaped guide catheter (235), while holding the stiffening mandrel (280) stationary, the shaped or curved region (245) will form a "U" shaped curve as shown in FIG. 10C. The proximal end (305) of the curved or shaped region (245) is aligned with the junction (300) of the stiffening mandrel (280). Withdrawal of the stiffening mandrel (280) and sheath (270) then places the curved region (245) of the shaped guide catheter (235) at a location within the vessel to allow advancement of a therapeutic catheter within its lumen. The stiff curved region (245) will hold the curved shape during therapeutic catheter advancement.

Following the therapeutic procedure and removal of the therapeutic catheter, the sheath (270) is reintroduced into the shaped guiding catheter (235). The stiffening mandrel (280) is then advanced within the sheath (270) to a location that aligns the transition (300) junction of the mandrel with the proximal end (305) of the shaped guide catheter (235) curved region (245). While holding the stiffening mandrel (280) fixed in space, the shaped guide catheter (235) is then withdrawn while holding the stiffening mandrel (280) stationary. The shaped guide catheter and stiffening mandrel (280) are then withdrawn followed by the sheath (270).

In use, the shaped guide catheter (235) can be delivered from the brachiocephalic artery, form a loop in the aorta and extend back into the brachiocephalic artery. Alternately the guide catheter can be delivered from the left subclavian artery and extend into the left common carotid artery using the methods described in FIGS. 10A-10D.

Figure 11A:
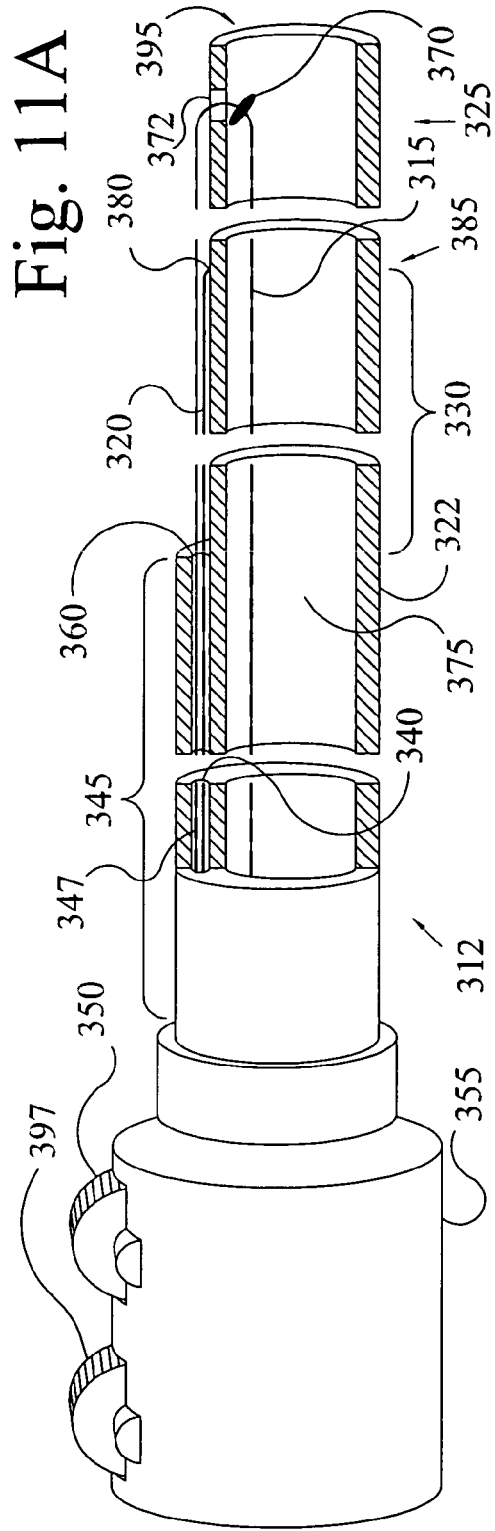
FIG. 11A shows a sectioned view of an access guide catheter with a removable steering fiber.

Another embodiment for the looped access guide catheter (312) having a closed loop conformation as described earlier is shown in FIGS. 11A-11C. This embodiment uses two fibers to form the closed loop, a steering fiber (315) and a cinch fiber (320). The access guide catheter (312) is comprised of a catheter shaft (322) having a flexible distal region (325) and a more supported loop region (330) located proximal to it. The catheter shaft (322) can be a dual lumen extrusion as shown in FIG. 11A or it can be a single lumen extrusion. A steering fiber (315) runs through the fiber lumen (340) of the contained region (345) and then extends on the outside of the catheter shaft (322) in the loop region (330). The control end (347) of the steering fiber (315) passes through a control element (350) located near or on the manifold (355). The control element (350) provides tension and locking control to the steering fiber (315). The steering fiber (315) passes through the fiber lumen (340), out of the fiber opening (360), and through a steering orifice (372) located near the distal end of the access guide catheter (312) and into the access lumen (375). A stop element (370) fixed to the steering fiber (315) and located within the access lumen (375) during tensioning of the steering fiber (315) will not pass through the steering orifice (372). The steering fiber (315) extends through the access lumen (375) and out of the manifold (355) of the access guide catheter (312). A cinch fiber (320) extends through the fiber lumen (340) and out of the fiber opening (360). The cinch fiber (320) attaches to the attachment point (380) at or near the distal end (385) of the loop region (330).

As the steering fiber (315) is tensioned and held by the steering control element (350), the flexible distal region (325) forms a loop region (330) as shown in FIG. 11B. This allows the distal end (395) of the flexible distal region (325) to be pulled back into the ostium of the vessel from which it came as will be shown later. Tension can now be applied to the cinch fiber (320) via tensioning element (397) shown in FIG. 11A while advancing the catheter shaft (322) distally forming a closed loop (399) as shown in FIG. 11C. The flexible distal region (325) will advance distally down the delivery vessel. The steering fiber (315) can be removed from the access guide catheter (312) by pulling on the removal end (400) of the steering fiber (315).

This embodiment allows a closed loop (399) to be placed in the aorta to allow deliver and support for a therapeutic or diagnostic catheter or procedure from the brachiocephalic artery back in an opposing direction to the brachiocephalic artery. The flexible distal region (325) extends a few centimeters down the brachiocephalic artery for making a smooth transition from the loop region (330) into the vessel.

Figure 12A:
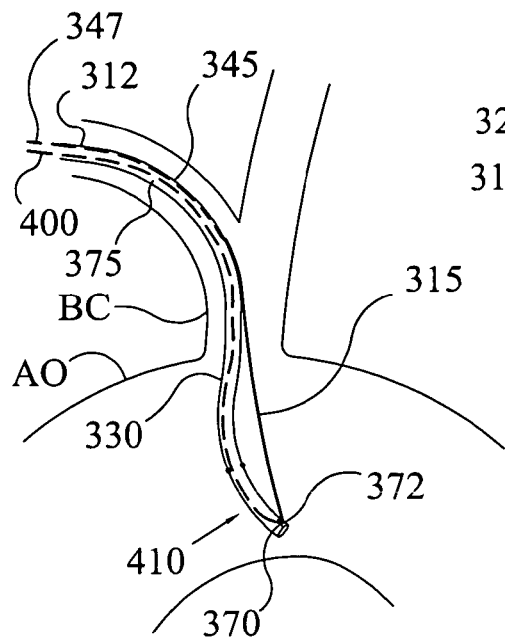
FIGS. 12A-12D show views of an embodiment of the access guide catheter being delivered to the brachiocephalic artery.
Figure 12B:
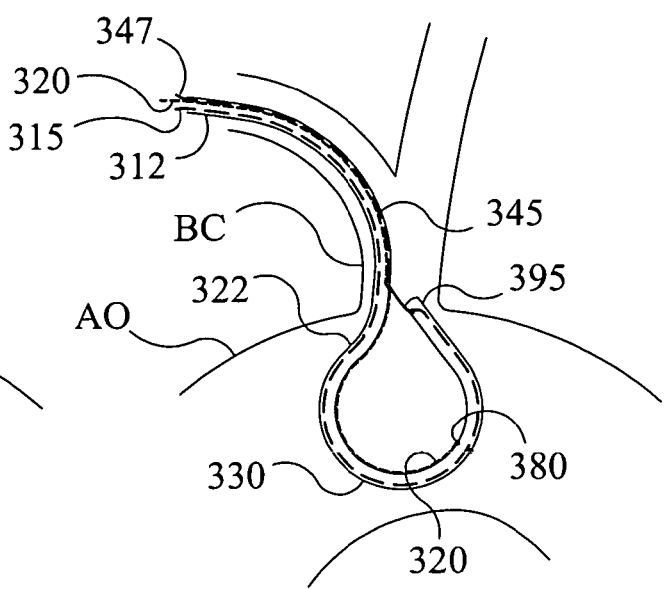
Figure 12C:
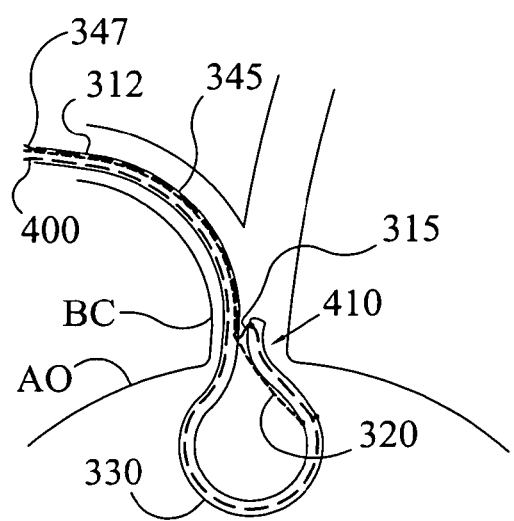
Figure 12D:
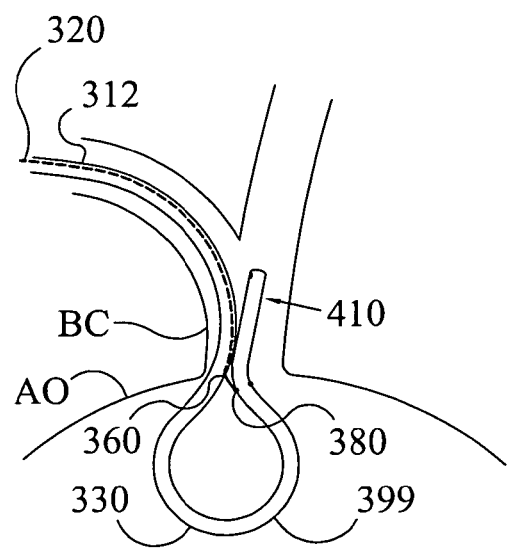

FIGS. 12A-12D show the method of use for this embodiment. The access guide catheter (312) is introduced into the radial artery and is advanced into the aorta (AO) as shown in FIG. 12A using a guidewire in the access lumen (375) to aid in advancement through the vasculature. The guidewire is then retracted back into the access guide catheter (312). The control end (347) of the steering fiber (315) is then tensioned causing the flexible region (410) of the access guide catheter (312) to form a loop as shown in FIG. 12B. The stop element (370) on the steering fiber (315) cannot pass through the steering orifice (372) located near the distal end (395) of the access guide catheter (312). The catheter shaft (322) of the guide catheter (312) is then advance distally while holding the cinch fiber (320) stationary to form a loop in the loop region (330) of the access guide catheter (312) as shown in FIGS. 12B and 12C. Tension is then applied to the cinch fiber (320) to pull the attachment point (380) into proximity with the fiber opening (360) to form a closed loop (399) in the loop region (330) as shown in FIG. 12D. The steering fiber (315) can be removed by pulling the removal end (400) of the fiber (315) and removing it from the access lumen (375). The access guide catheter (312) is positioned in the aorta with the flexible region (410) extending into a portion of the brachiocephalic artery. The access lumen (375) is available for passage of a therapeutic catheter. This technique can be applied to other vessels that require delivery from one vessel back into the same vessel from which it originated in an opposing direction.

The access guide catheter of FIGS. 1A-1D, 11A-11C, and 12A-12D can be used on the left or the right side great vessels without following over a sheath or guidewire that extends continuously from the access vessel such as the brachiocephalic artery or left subclavian artery to the delivery vessel such as the brachiocephalic artery or left common carotid artery. The access guide catheter can advance over a guidewire directly to the aorta. It is noted however that to ensure a smooth transition between the guidewire (typically a 0.035 guidewire) and the guide catheter, a tapered sheath may be placed within the access catheter during its placement.

One embodiment of a tapered sheath (415) is shown in FIG. 13 which shows a tapered sheath (415) having an outer diameter that fits closely within the access guide catheter (5) throughout most of its shaft length. The inner diameter can be larger than the guidewire (420) diameter to allow space for contrast delivery from the contrast inlet (417) through the sheath lumen (418) between the tapered sheath (415) and the guidewire (420). To deliver contrast through the lumen of the tapered sheath (415), the guidewire (420) is partially retracted back into the tapered sheath (415) to provide a pathway for contrast to flow out of the end of the tapered sheath. The tapered sheath (415) is flexible and typically removed once the access guide catheter (5) has been placed within the appropriate great vessel. The tapered sheath (415) can have a beveled recess (425) such that when the guidewire (420) is pulled back partially within the sheath lumen (418) for angiographic contrast delivery, the guidewire (420) can be advanced again out of the tapered sheath (415). Alternately, the tapered distal end (430) can have one or more perfusion holes (435) to allow exit for contrast medium.

Alternately the tapered sheath (415) can be constructed to provide a smaller outer diameter throughout most of its shaft length and contrast can be delivered through an annular space between the tapered sheath (415) and the access guide catheter (5).

An alternate embodiment of the access guide catheter is shown in FIGS. 14 and 15. This access guide catheter (440) has a preformed flexible tip region (445) and a preformed stiffer region (450) with a curved shape to aid in providing access from the left subclavian artery to the left common carotid artery. It is noted that the stiffer region (450) is still less stiff than the shaft for a standard guide catheter. A somewhat altered preformed shape can be applied to provide access from the brachiocephalic artery back into the brachiocephalic artery. Alternately one could use the access guide catheter (440) of this embodiment or other embodiments of this invention to provide access from the left subclavian artery to the brachiocephalic artery or from the brachiocephalic artery to the left common carotid artery.

The access guide catheter (440) of the embodiment shown in FIGS. 14 and 15 has a proximal region (455), a flexible tip region (445), and a stiffer region (450) located in between that has a stiffness that is greater than the flexible tip region (445). The stiffer region (450) comprises a portion of the loop region (460) of the access guide catheter (440) that is located between the attachment point (470) and the proximal fiber opening (475). The flexible tip region (445) comprises at least a portion of the distal region (480) that extends distally from the attachment point (470) to the distal end (485) of the access guide catheter (440). The steering fiber (490) extends from its control end (495) down one lumen of the shaft of the access guide catheter (440). As shown it extends down the access lumen (500) although it could also have extended down the fiber lumen (505) or another lumen. Near the distal end (510) of the stiffer region (450), the steering fiber (490) exits through a distal fiber opening (515) and follows along the external side of the access guide catheter (440) shaft before reentering the steering orifice (520) and passing back proximally up the access lumen (500). A stop element (525) is located on the steering fiber (490) within the access lumen (500) near the steering orifice (520) that will not pass through the steering orifice (520). As tension is placed on the control end (495) of the steering fiber (490), the flexible tip region (445) forms a curve that will help direct a guidewire or other member into the vessel that is being delivered to from the aorta as shown in FIG. 15. As shown in this embodiment, the steering fiber (490) can be removed by applying tension to the removal end (527) of the steering fiber (490) and pulling it out of the access lumen (500). It is noted that the steering fiber (490) could have been attached to the flexible tip region (445) at a location similar to that for the steering orifice (520) and perform the same function except that it would not be removable.

A cinch fiber (530) extend through a fiber lumen (505) and out of a proximal fiber opening (475) near the proximal end (535) of the stiffer region (450) where it follows along the outer surface of the access guide catheter (440) shaft and attached onto the access guide catheter (440) shaft at the attachment point (470) located near the distal end of the stiffer region (450). In one embodiment the attachment point (470) is located on the opposite side of the access guide catheter (440) shaft such that the direction of the loop generated by the cinch fiber (530) is in a different direction to the curve created by the steering fiber (490). Applying some tension on the cinch fiber (530) the attachment point (470) moves closer to the proximal fiber opening (475) as shown in FIG. 15. As more tension is applied to this fiber, the access guide catheter (440) will form a curve as the attachment point (470) is brought into close proximity or touching the proximal fiber opening (475) forming a closed loop. This closed loop can be pulled into contact with the upper wall of the aorta (AO) by placing tension onto the proximal end of the access guide catheter (440) shaft to provide support for subsequent catheters that are introduced into the access lumen (500). It is noted that the cinch fiber (530) could have passed through the access lumen (500) or through another passage as identified earlier.

The wall structure for this access guide catheter can be a braided polymeric monolumen or duel lumen tubing. Alternately one can form one layer of the access guide catheter shaft from a thin metal tubing that has been etched away to form a fibrous pattern having circumferential componency to retain flexibility and yet provide anti-kink character and torqueablity. The metal layer can be coated with a polymeric layer via spraying, dip coating, extrusion, or other deposition process. The metal layer can be formed via machining with a cutting wheel, laser machining, chemical etching, or other suitable process. The preformed curved regions can be formed via thermal, solvent, or other processing methods use to form polymers and metals. An inner polymeric liner can be used to provide smoothness and lubricity to the lumen of the access guide catheter.

The method of use for this embodiment is shown in FIGS. 16A-16C for access from the left subclavian (LSC) to the left internal carotid artery (LIC). It is noted that similar method could be applied from brachiocephalic to brachiocephalic artery or to other tubular members of the body. The access guide catheter (440) enters the aorta (AO) from the left subclavian artery (LSC) over a guidewire (540) such as a 0.035 guidewire. The guidewire (540) is retracted and the steering fiber (490) is tensioned to form a curve in the flexible tip region (445) as shown in FIG. 16A. The cinch fiber (530) is tensioned to pull the attachment point (470) closer to the proximal fiber opening (475) as shown in FIG. 16B. The cinch fiber (530) is further tensioned to bring the attachment point (470) into contact with the proximal fiber opening (475) and having the flexible tip region (445) directed toward the ostium to the left common carotid (LCC). A closed loop region (545) is formed in the access guide catheter (440). The guidewire (540) can be advanced into the left common carotid artery (LCC). The shaft of the access guide catheter (440) is then tensioned proximally to advance the flexible tip region (445) into the left common carotid (LCC) and pull the stiffer region (450) of the access guide catheter (440) into contact with the upper wall of the aorta (AO) for support as shown in FIG. 16C. The steering fiber (490) can be removed from the access guide catheter (440) by applying tension to the removal end (527) of the fiber. A tapered sheath can be advanced over the guidewire if desired to provide for a taper between the guidewire and the access guide catheter and also to deliver contrast more distally in the carotid artery if desired.

Figure 17A:
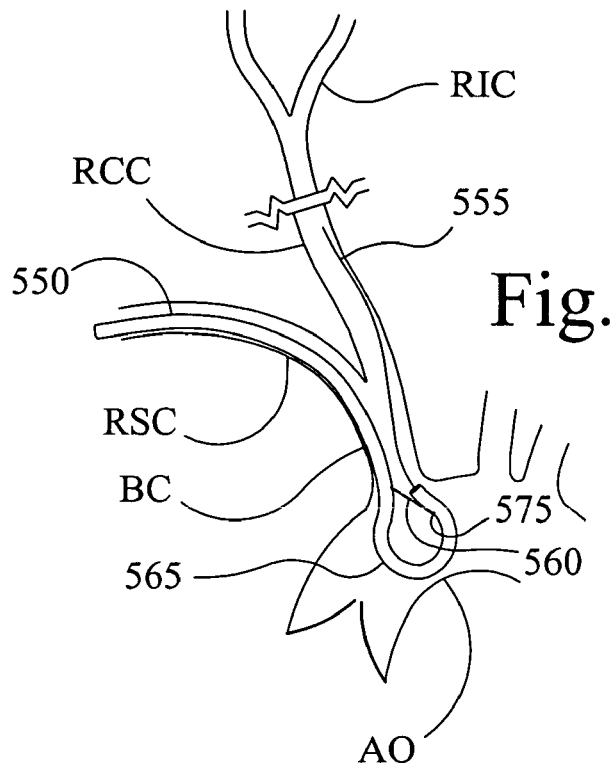
FIGS. 17A-C are views of the access guide catheter extending from the brachiocephalic artery back into the brachiocephalic artery forming a closed loop.
Figure 17B:
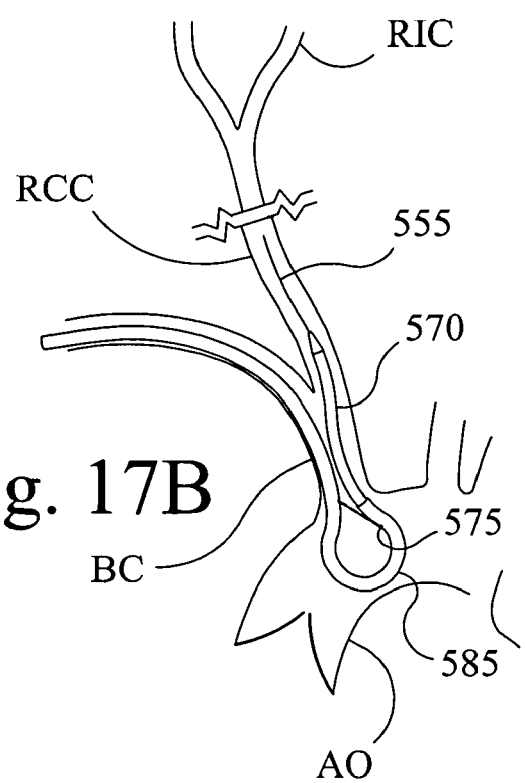
Figure 17C:
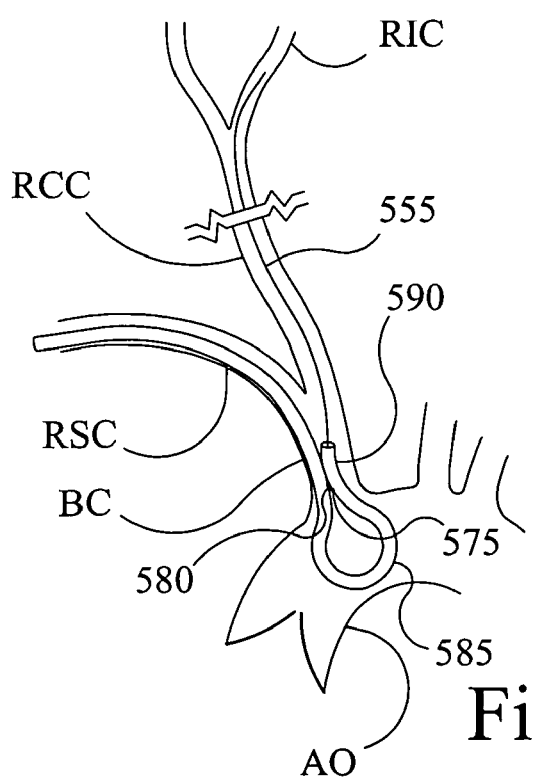

FIGS. 17A-C show how the access guide catheter (550) of this invention can be used to deliver an angiogram and a therapeutic catheter from the brachiocephalic artery (BC) to the brachiocephalic artery (BC) and finally to the right common (RCC) and right internal carotid artery (RIC). The access guide catheter (550) enters the aorta (AO) over a guidewire (555). The fiber (560) is tensioned to place the loop region (565) into a partial loop as shown in FIG. 17A. A guidewire (555) can be advanced through the access guide catheter (550) into the brachiocephalic artery (BC). A tapered sheath (570) can be advanced over the guidewire (555) and within the access guide catheter (550) to provide a smooth transition from the wire (555) to the access guide catheter (550) as shown in FIG. 17B. The tapered sheath (570) can also be advanced along with the guidewire (555) to the right common carotid artery (RCC) if desired. An angiogram can be taken with contrast delivered through the tapered sheath (570) with the guidewire (555) partially withdrawn or through the access guide catheter (550). The fiber (560) can be further tensioned to place the attachment point (575) into contact with the fiber opening (580) to form a closed loop (585) as shown in FIG. 17C. The distal region (590) is located in the left common carotid artery ((LCC). The tapered sheath (570) and guidewire (555) can be removed and an embolic protection filter can be advanced early through the access guide catheter (550) to a site distal to the carotid lesion. A therapeutic catheter such as a stent delivery system can be advanced within the access guide catheter (550) and over the filter wire to the site of the lesion.

Figure 18A:
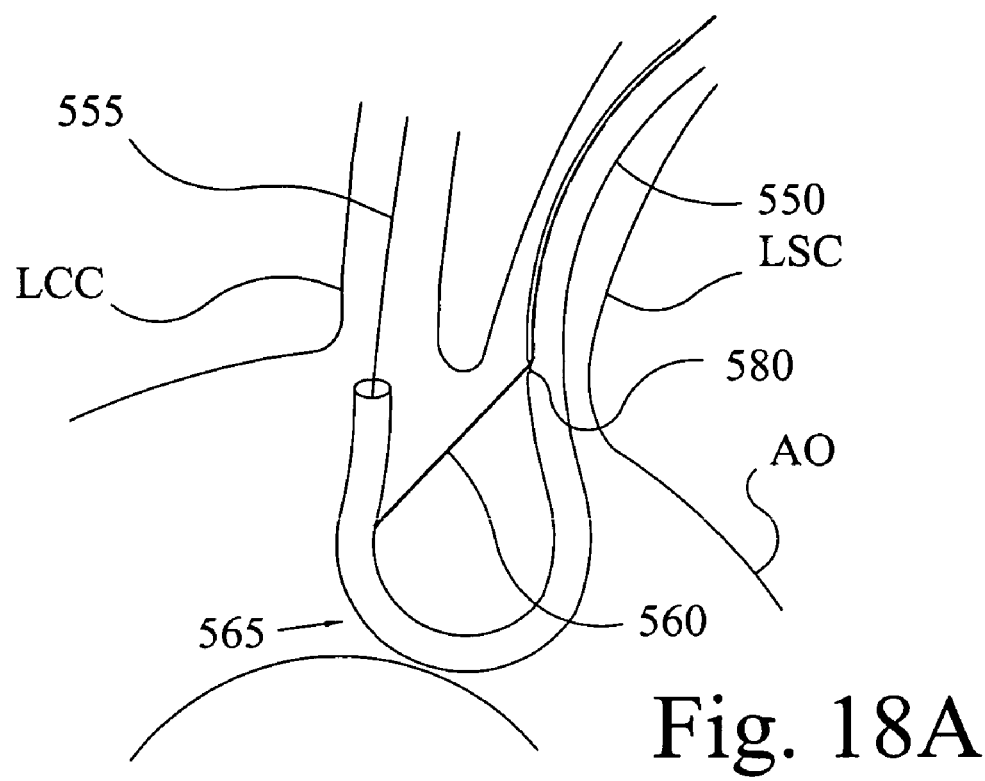
FIGS. 18A-18B are view of an embodiment of the access guide catheter extending from the left subclavian artery into the left common carotid artery.
Figure 18B:
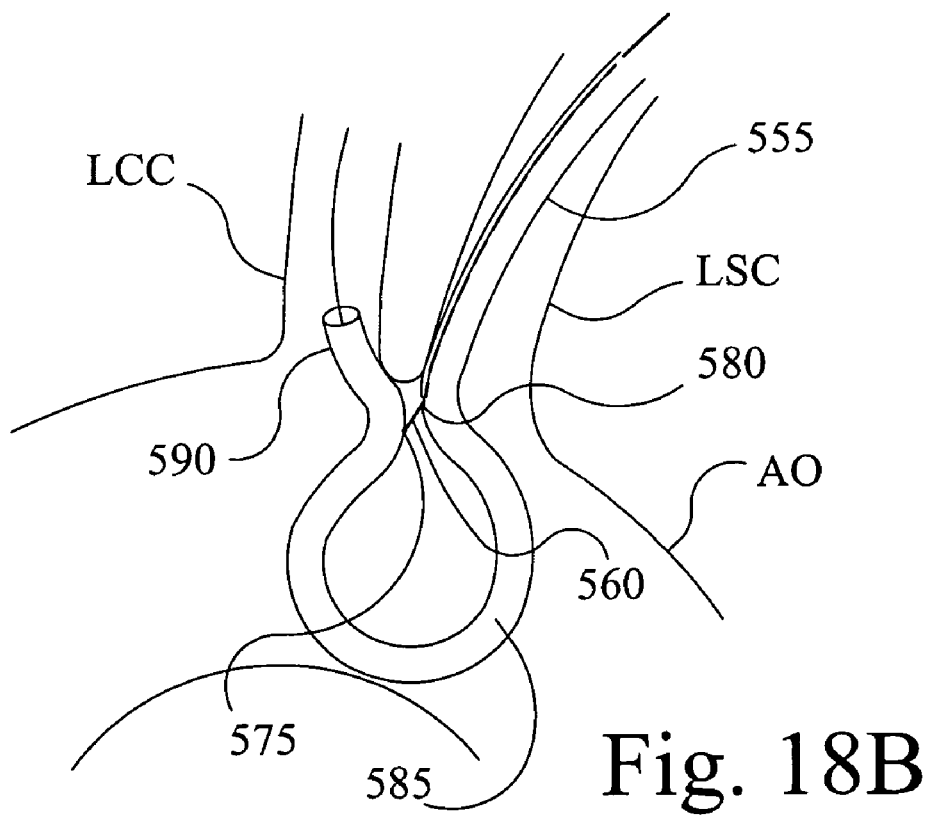

FIGS. 18A-18B show how the catheter of the embodiment shown in FIGS. 1A-1C and other embodiments can also be used to provide access from the left subclavian artery (LSC) to the left common carotid artery (LCC). FIG. 18A shows the access guide catheter (550) entering the aorta over a guidewire (555) and the fiber (560) being tensioned to place the loop region (565) into a curved shape. The access guide catheter (550) is then turned or torqued to align the distal end of the catheter (590) with the ostium of the left common carotid artery (LCC). A guidewire (555) is advanced into the left common carotid artery (LCC) and the distal region (590) of the access guide catheter (550) is advanced over the guidewire (555) into the left common carotid artery (LCC). A tapered sheath can be used to assist advancement of the access guide catheter (550) by forming a smooth transition between the guidewire (555) and the access guide catheter (550). The fiber (560) is further tensioned to pull the attachment point (575) into contact or proximity to the fiber opening (580) as shown in FIG. 18B. The guidewire (555) can be partially withdrawn to take an angiogram. Upon removal of the guidewire (555) and tapered sheath, an embolization protection filter can be advanced within the access guide catheter (550) to a site distal to the carotid lesion. The therapeutic catheter can then be advanced within the access guide catheter (550) and delivered to the carotid artery for treatment. The closed loop (585) formed in the distal region provides support for the therapeutic catheter as tension is applied to the catheter shaft of the access guide catheter (550).

Figure 19:
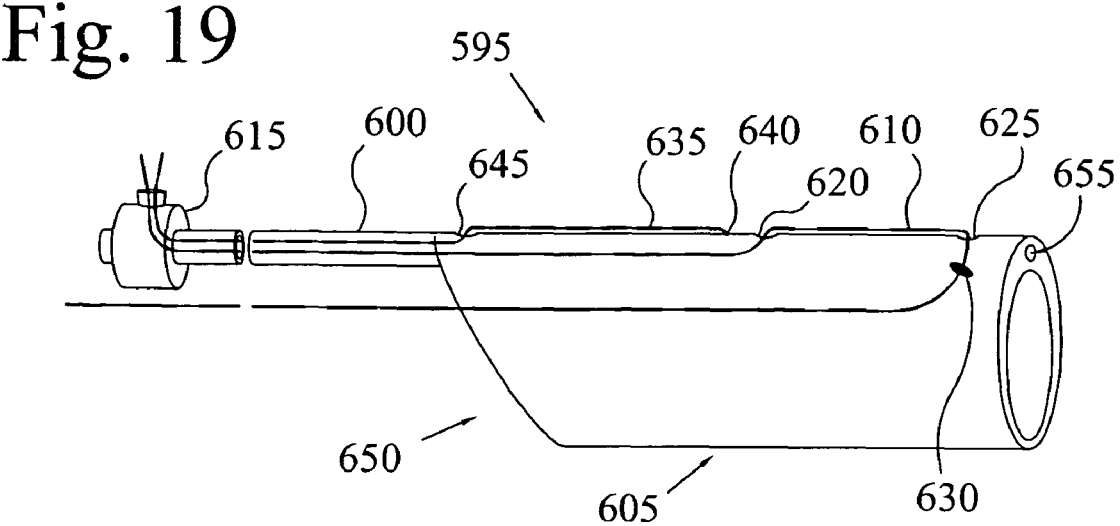
FIG. 19 is a partially sectioned view of the access guide catheter as a rapid exchange embodiment.

A first embodiment for a rapid exchange access guide catheter (595) is shown in FIG. 19. The catheter has a proximal element (600) connected to a distal guide segment (605). The distal guide segment (605) can be constructed in a manner similar to that described in the referenced provisional applications. As shown a steering fiber (610) extends from the manifold (615) through the proximal element (600) and exits the distal opening (620). It continues distally on the outside of the rapid exchange access guide catheter (595) and reenters the steering orifice (625) where it attaches to a stop (630) that will not fit through the steering orifice (625). The steering fiber (610) extends back proximally to the manifold (615). The steering fiber (610) provides the rapid exchange access guide catheter (595) with an ability to form a steering curve in the distal region of the guide segment (605). The rapid exchange access guide catheter (595) also has a cinch fiber (635) that is attached distally to an attachment point (640) and runs proximally along the outer surface to the proximal fiber opening (645) and into the proximal element (600) where it extends to the manifold (615). The cinch fiber (635) allows the attachment point (640) to be pulled into contact with the proximal fiber opening (645) to form a closed loop. The guide segment (605) contains similar regions to that described in previous embodiments.

The proximal opening (650) to the guide segment (605) is beveled to allow the distal guide segment (605) of the rapid exchange access guide catheter (595) to be removed from the introducer sheath upon withdrawal of the rapid exchange access guide catheter (595). The rapid exchange access guide catheter (595) can be constructed such that it does not have the cinch (635) and steering fibers (610). Instead the guide region can have no fibers and can have a thermally formed distal region with a straight or curved shape. A contrast dye lumen (655) can be configured to run all the way from the manifold (615) through the proximal element (600) and through a dye lumen located in the distal guide segment (605) or portion.

Another means of delivering contrast to a region distal of the distal guide region is via a tapered sheath having a recessed space and perfusion holes that provide passage for contrast delivery as described in FIG. 13. The tapered sheath is able to follow over a guidewire. Alternately, the tapered sheath can be made as a monorail sheath having a monorail entrance for the guidewire in order to obviate the need for exchange length guidewires when possible. The distal part of the tapered sheath follows over the guidewire and the proximal part runs adjacent to the guidewire. The distal guide segment of the guide catheter slidably fits over the tapered sheath.

Figure 20:
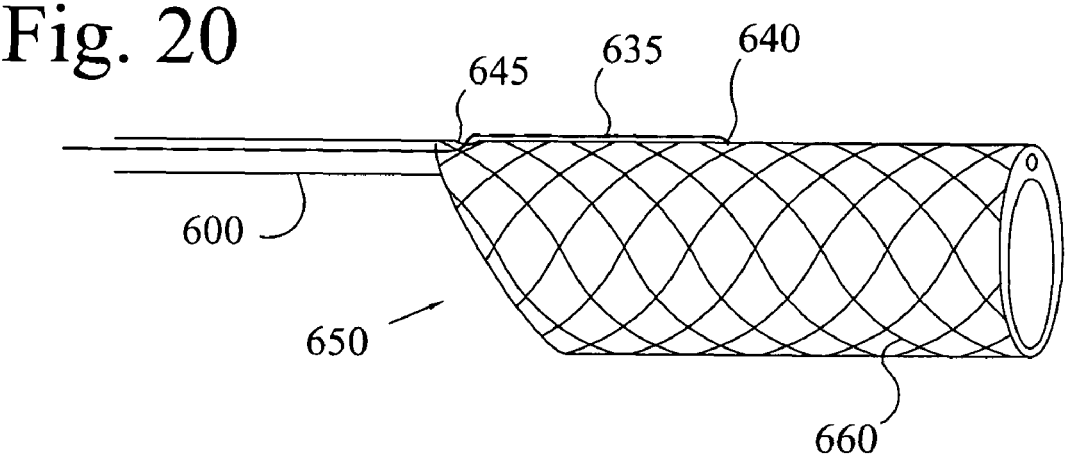
FIG. 20 is a partially sectioned view of the access guide catheter having a braided distal guide segment capable of reducing in diameter.

An alternate embodiment which has a passively expandable guide segment is shown in FIG. 20. The distal guide segment (605) is formed with a braided structure (660) found within the wall of this region. The braid (660) provides a bias for the distal guide segment (605) to stay in the larger diameter state. The distal guide segment (605) is forced into a smaller diameter conformation for delivery through the introducer. Once the distal guide segment (605) exits the introducer and is located in the blood vessel, the distal guide segment (605) expands to a larger diameter such that the largest aspect of the therapeutic catheter will freely fit through it. The other elements of this embodiment are similar to previous embodiments with a cinch fiber (635), a fiber opening (645), and an attachment point (640).

Figure 21:
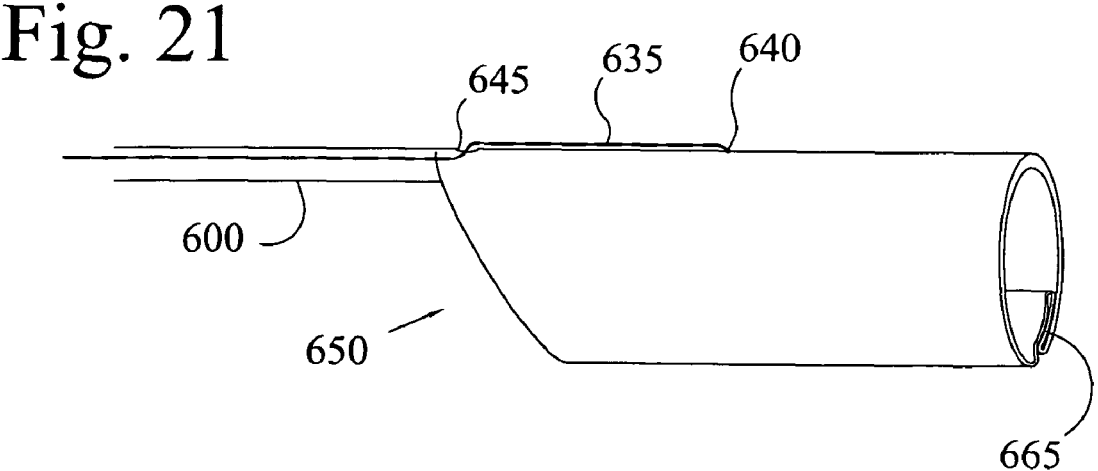
FIG. 21 is a partially sectioned view of an alternate embodiment of a rapid exchange guide catheter having a distal guide segment that reduces in diameter.

Another means for forming a passive expandable distal guide segment is shown in FIG. 21. In the distal guide segment (605) the tubing can be thinned along an axial line. During delivery through the introducer, the thin walled region can form a thin overlap (665). After the distal guide segment (605) has exited the introducer, it springs open to form a larger diameter.

FIGS. 22-25 show additional primary embodiments for the present access guide catheter invention having a closed loop conformation. Much of the structure of the catheters have been described in the earlier figures and will therefore not be repeated; instead focus will be given to describe the differences in the following embodiments that are found in the distal portion of the access guide catheter shaft which includes the loop region and portions of the catheter near the loop region.

As discussed earlier in FIG. 1D an external sheath (80) can be provided on the outside of the access guide catheter in order to allow the fiber opening to be moved along the axial length of the access guide catheter as the distal loop is being formed. This allows a small controlled loop to be formed within the aorta without contact of the cinch or steering fibers or the access guide catheter with the potentially friable atheromatous plaque located in the aorta or the Great Vessels that stem off of the aorta. Aside from using an external sheath the following embodiment will show ways of effectively providing a movable fiber opening by employing one or more releasable fiber openings with similar benefits to the movable external sheath.

Furthermore it is advantageous to provide the access guide with a movable attachment point or points. This allows the access catheter to begin the step of forming a loop with the attachment located near the distal end in order to form a tight loop. Once the loop is formed it is desirable to extend the access guide catheter distal end further into the ostium of the Great Vessel in order to ensure that it is properly seated and will not back out during the delivery of the therapeutic catheter. Additionally, it is beneficial to provide angiographic delivery to the carotid arteries without loss of contrast to the more proximal vessels that come off of the Great Vessel such as the right subclavian vessel to the arm or other vessels.

Figure 22:
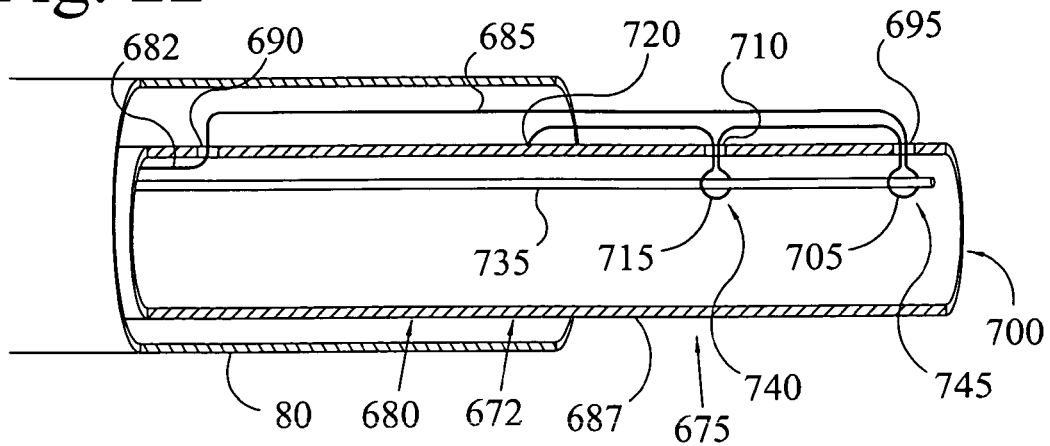
FIG. 22 is a partially sectioned view of the distal region of an access guide catheter positioned within an external sheath.

FIG. 22 shows a portion of the access guide catheter (672) comprising the distal region (675) and the loop region (680). The control end (682) of a steering-cinch fiber or common fiber (685) extends from within the catheter shaft (687) through the fiber opening (690) and distally into orifice B (695) located near the distal end (700) of the access guide catheter (672). The common fiber (685) then travels back out of orifice B (695) forming loop B (705) within the catheter shaft (687). The common fiber (685) extends in a proximal direction into orifice C (710) where it forms loop C (715) within the access guide catheter (672) and extends outside the access guide catheter (672) further proximally to permanent attachment D (720). Loop B (705) and Loop C (715) provide releasable attachment points that allow the point of attachment to interact consecutively and translate its location along the access guide catheter (672) distal region (675). A cinch release member (735) extends within the catheter shaft (687) and through loop C (715) forming releasable attachment C (740), and extends further distally through loop B (705) forming releasable attachment B (745). Application of tension on the proximal end of the cinch release member (735) causes releasable attachment B (745) to be released; further tensioning causes releasable attachment C (740) to be released. More openings can be formed in the access guide catheter (672) shaft and additional releasable loops can be formed in the common fiber (685) in addition to loops B and C if desired. It is noted that the cinch release member (735) can be a wire or fiber as shown in FIG. 22 or it can be a fiber that follows a knitted pattern that releases the attachment sites B (745) and C (740) by a zipping-type action as generally observed in the unzipping of a fiber from a knitted cloth with very low actuation force. Such a cinch release member can release the releasable attachment site B (745) first without being affected by the friction or other affects of any additional releasable attachment sites.

Figure 23A:
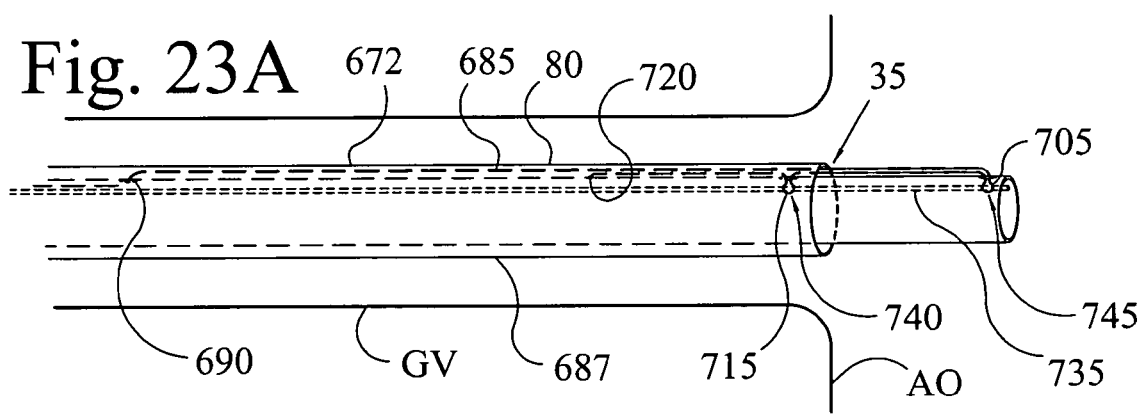
Figure 23B:
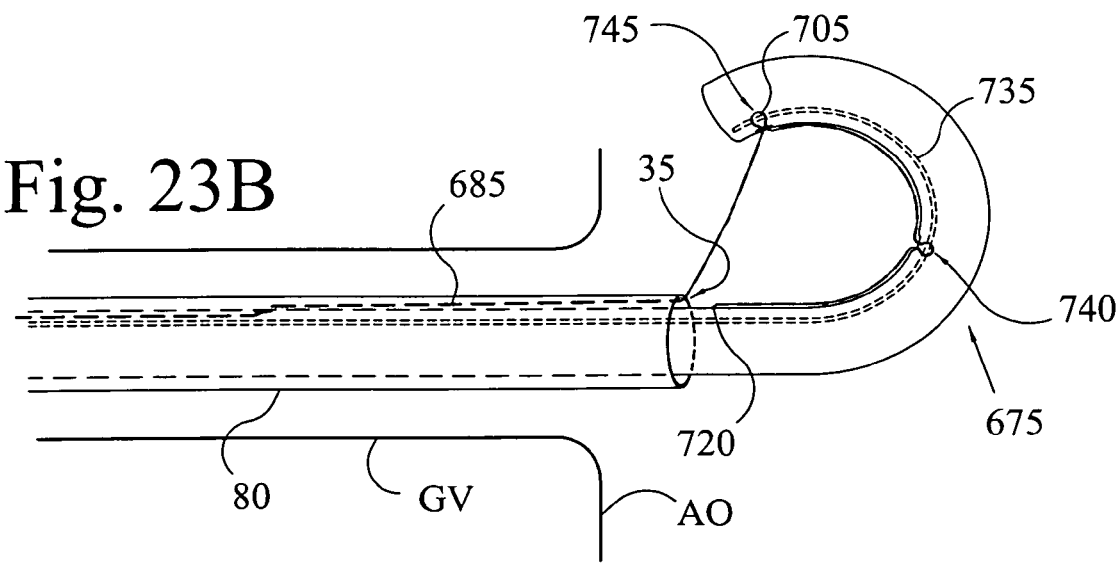

The method of use for the access guide catheter (672) can be shown in FIGS. 23A-23E. In FIG. 23A the access guide catheter (672) is passed, for example, from a Great Vessel (GV) into the aorta (AO). An external sheath (80) is located over the access guide catheter (672) with the end of the sheath (80) positioned between the releasable attachment point B (745) and permanent attachment point D (720). The cinch release member (735) is passed through loops B (705) and C (715) located at releasable attachment B (745) and C (740). The common fiber (685) passes through the fiber opening (35) located at the distal end of the sheath (80). The common fiber (685) is placed into tension via a tension element located at the manifold of the access guide catheter (672) causing the distal region (675) to form a loop within the aorta (AO) as shown in FIG. 23B. The external sheath (80) is withdrawn proximally as the common fiber (685) is being tensioned such that the sheath (80) end acting as a movable fiber opening for the common fiber (685) that has translated its position near to the permanent attachment D (720).

The access guide catheter (672) is advanced distally and the external sheath (80) can be further withdrawn proximally as shown in FIG. 23C. The cinch release member (735) is then withdrawn via a withdrawal element located on the access guide catheter manifold such that it no longer extends through loop B (705) allowing releasable attachment B (745) to disengage. The withdrawal element can be a spool or means to pull the release member out of the catheter shaft (687). The control end (682) of the common fiber (685) is placed into tension to pull the distal end (700) of the access guide catheter (672) further into the Great Vessel (GV) as the fiber opening (690) and access guide catheter (672) shaft are advanced distally into the aorta (AO) as shown in FIG. 23D.

The cinch release member (735) is further withdrawn such that it no longer extends through loop C (715) disengaging releasable attachment C (740) allowing the common fiber (685) to extend to permanent attachment point D (720). The common fiber (685) is again placed into tension to pull the distal end (700) of the access guide catheter (672) even further into the Great Vessel (GV) as the access guide catheter (672) shaft and the fiber opening (690) is advanced distally into the aorta (AO) as shown in FIG. 23E. The permanent attachment point D (720) is placed into approximation with the fiber opening (690) and forms a closed loop (750). The loop is ready for delivery of a filter wire and a therapeutic catheter such as a stent delivery system. The distal region (675) of the access guide catheter (672) is fully seated into the Great Vessel (GV) providing a stable seat and allowing delivery of contrast medium and passage for other catheters to the carotid artery or other desired artery.

An alternate embodiment of the access guide catheter (672) that does not require the use of an external sheath is shown if FIGS. 24A and 24B. In FIG. 24A the control end (682) of the common fiber (685) extends out of the fiber opening (690) in a distal direction and wraps around a steering holding member (755) forming a releasable fiber opening (690) between loop E (760) and loop F (765). The common fiber (685) extends distally through orifice B (695) where it forms loop B (705) within the catheter shaft (687) and extends back out of orifice B (695). The common fiber (685) extends proximally to orifice C (710) and forms loop C (715) then further extends proximally to permanent attachment D (720) as described previously in FIG. 22. The steering holding member (755) is a filament or fiber or other means that extends along the catheter shaft (687) and extends into orifice F (770) and forms loop F (765) within the catheter shaft and extends back out of the orifice F (770) and further distally into orifice E (775) within the catheter shaft, forming loop E (760), and then extends back out of the orifice E (775). The steering holding member (755) extends proximally to the manifold on the access guide catheter (672) and is held and controlled by a holding element. The control of the common fiber (685) requires it to be pulled a controlled amount to cause the distal region (675) of the access guide catheter (672) to form a loop. A steering release member (780) extends within the catheter shaft (687) and through loops E (760) and F (765) to restrain the loops such that they remain within the access guide catheter (672) shaft. This steering release member (780) extends proximally to the manifold of the access guide catheter (672) to a release element that can pull the release member (780) in a controlled manner to release loops E (760) and F (765) of the steering holding member (755) and thereby disengage releasable attachments E (785) and F (790) respectively. The steering release member (780) can be a fiber formed from in a knitted pattern that can be unzipped by pulling on a thread to release loops E (760) or F (765) and thereby disengage releasable interlocks E (785) or F (790). A cinch release member (735) extends through loops B (705) and C (715) as described earlier in FIG. 22 forming releasable attachment point C (740) and releasable attachment point B (745) with the common fiber (685). The cinch release member (735) can be a fiber or a knitted filament as described earlier. It is noted that additional openings and attachments can be formed in the catheter shaft (687) for the steering holding member (755) to form a releasable interlock beyond the two described for orifice E (775) and F (770). As the steering release member (780) is withdrawn the fiber openings (690) are translated and interact consecutively along the catheter shaft.

In another embodiment shown in FIG. 24B the steering holding member (755) extends axially within the catheter shaft (687) and out of orifice F (770) and then back into orifice F (770) again forming loop F (765). It then extends axially and distally to orifice E (775). The steering holding member (755) extends out of orifice E (775) and then back into orifice E (775) again forming loop (760). A steering release member (780) holds the steering holding member (755) such that it forms a releasable loop on the outside of the access guide catheter (672). The common fiber (685) extends through loop F (765) and loop E (760) each of which form releasable fiber openings (690) on the outside of the access guide catheter (672). Withdrawal of the steering release member (780) allows loop E (760) and then loop F (765) to be released independently and thereby disengaging the releasable interlock E (785) and its associated fiber opening (690) or releasable interlock F (790) and its associated fiber opening (690) of the common fiber (685) from the catheter shaft (687). The cinch release member (735) along with releasable attachments B (745) and C (740) are the same as discussed previously in FIG. 24A.

The cinch release member (735) and steering release member (780) can be individual fibers, filaments, or members. It is understood that they can also be contiguous with each other such that they form a single contiguous fiber (795).

Figure 25A:
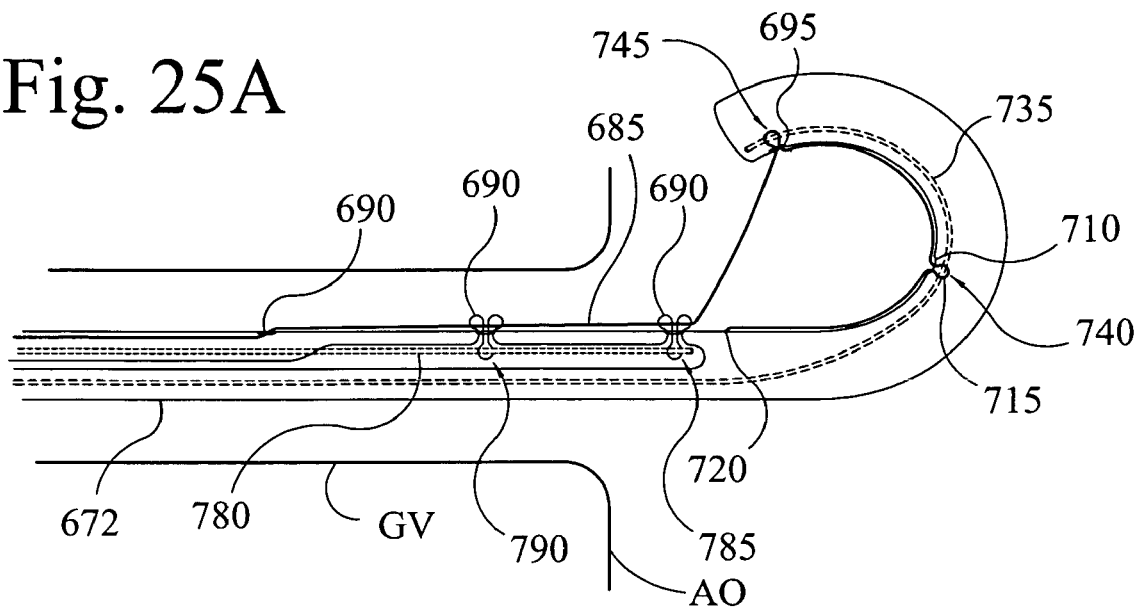
FIGS. 25A-D are views of an access guide catheter having releasable fiber openings and releasable attachment points extending from a great vessel into the aorta and back into the great vessel.
Figure 25B:
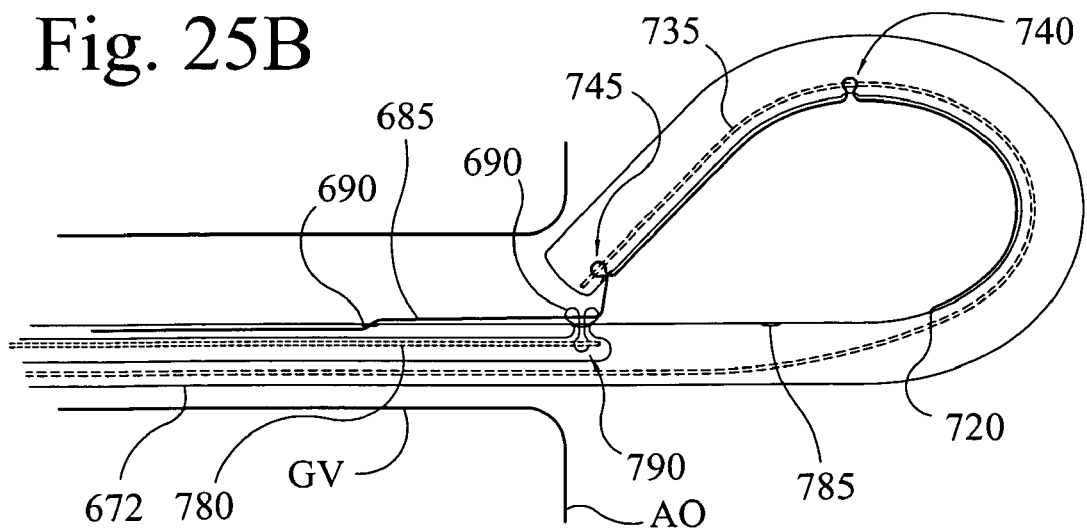

The method of use for the embodiments shown in FIGS. 24A and 24B is shown in FIGS. 25A-D. The access guide catheter (672) is advanced from the Great Vessels (GV) into the aorta (AO). The common fiber (685) which is slidably attached at releasable attachment E (785) is tensioned via the tension element at the manifold. The releasable attachment point B (745) is brought into approximation with releasable attachment E (785) as shown in FIG. 25A.

The steering release member (780) is pulled back via a release element at the manifold to release loop E (760) and releasable interlock E (785) and its associated fiber opening (690). Further tensioning of the common fiber (685) places releasable attachment point B (745) into approximation with releasable interlock F (790) as the catheter shaft (687) has been advanced distally into the aorta (AO) as shown if FIG. 25B.

Figure 25C:
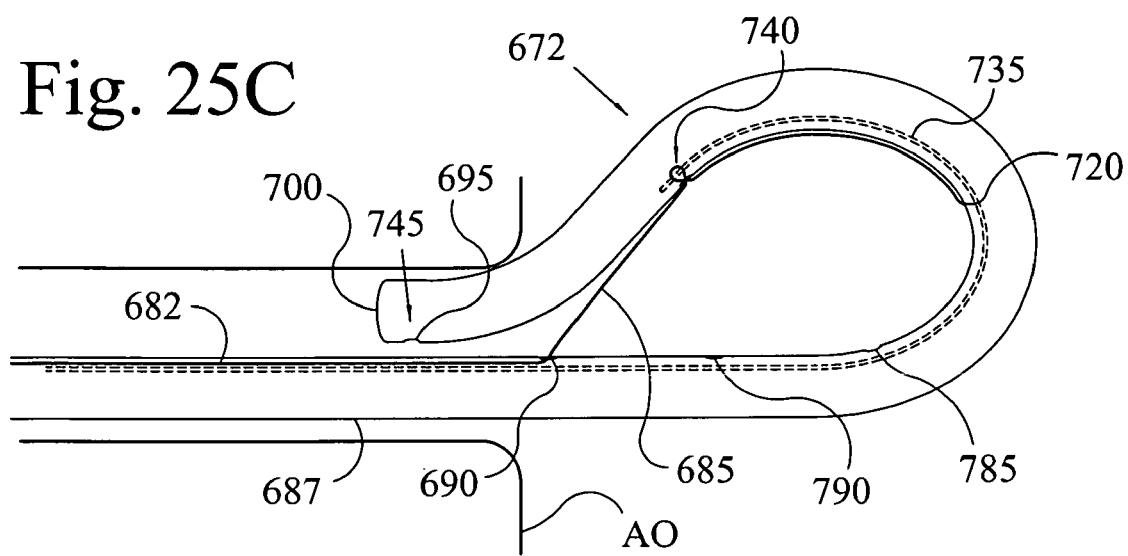
Figure 25D:
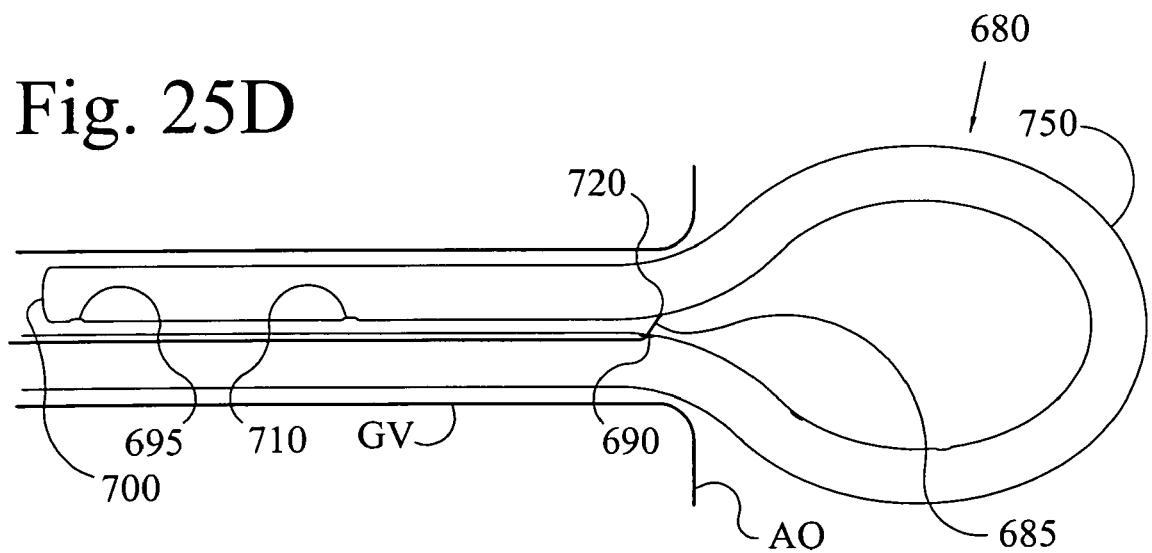

The cinch release member (735) can then be withdrawn via a release element located at the catheter manifold to release loop B (705) and releasable attachment B (745). The common fiber (685) is again tensioned to pull the distal end (700) of the access guide catheter (672) into the Great Vessel as the catheter shaft (687) is advanced distally as shown in FIG. 25C.

The cinch release member (735) is further withdrawn to release loop C (715) and releasable attachment C (740). Tensioning of the common fiber (685) pulls the distal end (700) of the access guide catheter (672) further into the Great Vessel (GV) with permanent attachment D (720) being placed into approximation with the fiber opening (690). The access guide catheter (672) is now formed into a closed loop (750) with the common fiber (685) or cinch fiber extending from permanent attachment D (720) into the fiber opening (690). The access guide catheter (672) is now ready for passage of contrast medium, delivery of a filter device, or passage of a therapeutic catheter through the access catheter.

The access catheter can be used to deliver other catheters, devices, or contrast medium to the carotid arteries as described above. Additionally, the access catheter can provide passage for delivery to the cerebral arteries and the vertebral arteries. Furthermore, it is noted that the present invention can also be used to provide passage around the iliac bifurcation off of the aorta. The present invention can be used in any tube of the body including veins, or non blood carrying ducts that require a passage in a reverse direction from which the catheter came. Also it can be used to gain access to ducts or tubes that require a 180 degree turn or nearly as tight of a turn to a vessel, opening, or an organ with adequate space for negotiating the turn.

The Great Vessels that exit off of the aorta to the head differ from the right side to the left. On the left side, the present invention can be used to enter the left common carotid artery from the left subclavian artery. Alternately the present invention can be used to provide access to the left common carotid artery from the brachiocephalic artery. To provide access from one vessel to another vessel including the same vessel in an opposed or nearly opposed direction a segmented mandrel placed within the access guide catheter can be used to provide a directional pathway for the access guide catheter to follow. The segmented mandrel is intended to be delivered in a soft and flexible state over a guidewire if a guidewire is needed to gain initial access to the desired vessel. Once the segmented mandrel has at least in part reached its location, the shape of the mandrel is created and fixed. Another catheter can then follow the fixed shape of the segmented mandrel and advanced over the mandrel. The segmented mandrel can be used for a variety of applications throughout the body. Whenever there is a sharp turn or a series of turns in a tubular member of the body a segmented mandrel will help to provide passage for another tubing that would pass over it.

A segmented mandrel (800) is shown in FIGS. 26A and 26B. It is made up of segments (805) which are formed out of a tubular shape such as the circular tube (810) shown in FIG. 26B. The cross-sectional shape can be round, oval, or other geometrical shape. From a side view the tube is cut into segments that are trapezoidal (815) in shape from a side view, a parallelogram (820) in side view, rectangular or square in side view, or some intermediate or other shape in side view. Generally, the segments (805) that are rectangular in side view are found located in the straight portions of the mandrel. The diameter of the circular tube (810) that forms each of the segments (805) is such that it fits easily within the access guide catheter (870) or catheter that is intended to follow over it. For a 6-7 French guide catheter the diameter of the segments is approximately 4-6 French or 1.3-2.0 mm. The diameter can be larger or smaller than this to direct catheters of varying sizes. The segments can be formed out of a metal tube such as stainless steel or nitinol or alternately from a polymeric tube such as polyimide, nylon, or other polymer of tensile strength necessary to support the catheter that must follow over it.

Inside each segment (805) are located two hypotubes, hypo 1 (825) and hypo 2 (830) positioned at opposite sides of each segment 180 degrees apart as shown in FIG. 26B and attached or joined to the segment (805) via a joint (835). The hypotubes can be located at other locations along the perimeter and more than two hypotubes can be used. The hypotubes are not required to be located 180 degrees apart from each other but can be adjusted to provide a shape to the mandrel that fits the anatomy that is being accessed. The joint (835) can be formed via welding, brazing, adhesive bond. The hypotubes can also be formed contiguously with each segment via an extrusion process that has multiple lumens. The hypo tube can be formed from either a metal or polymer similar to those described for the material for the segment. The diameter for each hypotube is such that each allows passage for a fiber or wire. For example, wire 1 (840) and wire 2 (845) pass within hypo 1 (825) and hypo 2 (830) respectively. It is anticipated that the wire can range in diameter from 0.003 to 0.010 inches and can be formed from metal or polymer and can be mono- or multi-filament. The gap between the two hypotubes is large enough to allow passage of a 0.035 inch guidewire or other guidewire through the guidewire lumen (847). An access guide catheter (870) or other catheter can then be passed over the segmented mandrel (800) and directed in any appropriate direction.

The segments (805) are then stacked onto wire 1 (840) and wire 2 (845) in a manner shown in FIG. 26A. The wires are attached to the distal segment (850) at the wire attachments (855). The wire attachments (855) can be formed via welding, brazing, adhesives, swaging, or other methods. The wires extend proximally to the manifold located at the proximal end of the segmented mandrel (800). Here a wire 1 tensioner (860) and a wire 2 tensioner (865) are located to provide tension to the respective wires when it is appropriate as described in FIGS. 27 and 28.

FIG. 27 shows the segmented mandrel (800) located within a catheter such as the access guide catheter (870) that will be delivered over the segmented mandrel (800). The tensioner located at the manifold has provided tension to wire 1 (840) causing the distal portion of the segmented mandrel (800) to form a first curve (872) of a desired shape as identified by the shapes of the individual segments (805) located in the distal portion (875) of the segmented mandrel (800). FIG. 28 shows the result of placing tension onto the manifold wire 2 (845). The shape of the mandrel segments (805) located just proximal to the distal portion (875) is designed to cause a bend in the segmented mandrel (800) and the surrounding access guide catheter (870) into a second curve (880) that is in an opposite direction. The overall shape of the segmented mandrel (800) can be generated by adjusting the shape given to the side view of each of the segments (805) such that one can provide the appropriate shape to fit the specific anatomy of the tubular member of the body being accessed. The proximal portion (885) of the mandrel (800) is not required to be made up of segments if this portion of the mandrel does not undergo significant bending. It is noted that more than two hypo tubes and wires can be employed in this invention to provide additional curvature to the mandrel.

Figure 29A:
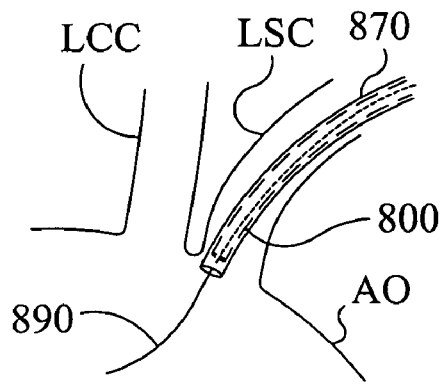
FIGS. 29A-D are views of the segmented mandrel positioned within an access guide catheter and forming two curves to provide access from the left subclavian artery to the left common carotid artery.
Figure 29B:
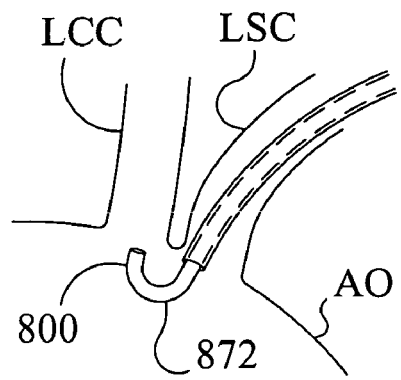
Figure 29C:
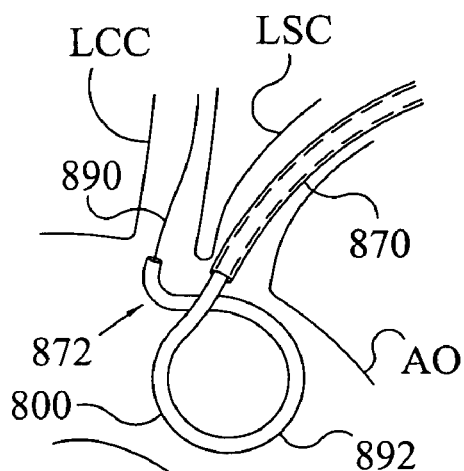
Figure 29D:
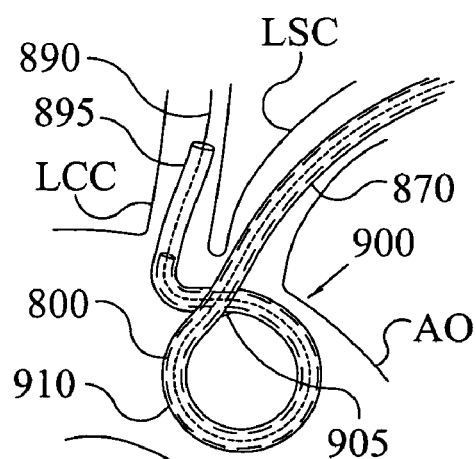

The segmented mandrel (800) can be used to place the access guide catheter (870) from the left subclavian (LSC) to the left common carotid (LCC) as described in FIGS. 29A-29D. Alternately, it can be used to provide access to other vessels of the body as described earlier. A 0.035 inch guidewire is advanced from the left subclavian artery (LSC) into the aorta (AO). The segmented mandrel (800) in its flexible state and the access guide catheter (870) are advanced over the guidewire (890) to the aorta (AO) as shown in FIG. 29A. The segmented mandrel (800) is fully torqueable such that it is aligned to direct its bending motion toward the left common carotid artery (LCC). The segmented mandrel (800) is advanced distally a small distance out of the access guide catheter (870) and wire 1 (840) of the segmented mandrel is placed into tension forming a first curve (872) on the distal end as shown in FIG. 29B. The segmented mandrel (800) is further advanced distally and wire 2 (845) is placed into tension to form a loop curve (892) as shown in FIG. 29C. The guidewire (890) can be advanced into the left common carotid artery (LCC). The access guide catheter (870) is then advanced over the segmented mandrel (800) such that the soft flexible distal region (895) extends into the left common carotid artery (LCC) over the guidewire (890). The stiffer portion (900) of the access guide catheter (870) is positioned adjacent to the left subclavian artery (LSC) as shown in FIG. 29D. Radioopaque markers positioned on the segmented mandrel (800) or access guide catheter (870) can ensure proper positioning of the catheter (870) and segmented mandrel (800) in an axial direction. FIG. 29D shows possible positions along the catheter that could define a stiffer portion (900) of the catheter, for example, as shown between the "x" and the "dot". The access guide catheter has a cinch fiber (905) or common fiber (685) that can then be tensioned to form a closed loop (910) as described earlier. Once the access guide catheter (870) is located properly within the left common carotid artery (LCC), the wire tensioning elements on the manifold of the segmented mandrel (800) are released allowing the segmented mandrel (800) to become flexible and withdrawn from the access guide catheter (870). The access guide catheter (870) is then ready for delivery of contrast to the carotid, delivery of the filter, and providing access for the therapeutic catheter or stent delivery system.

Other catheters including but not limited to the access guide catheter of this invention can also be used to travel externally along the outside of the segmented mandrel. Such catheters include any hollow tubular catheter that is required to undergo a curved path in order to extend from one portion of a first vessel to another portion of a second vessel. Such catheters can be used to deliver diagnostic or therapeutic devices or drugs to a more distal site within the tubular member. The body vessel can be any tubular member of the body including arteries, veins, the intestinal track, pulmonary trunk, gastric tubes, the esophagus, and others. The segmented mandrel can be introduced into the body in a flexible state within a catheter or over a guidewire. The wires and found in the segmented mandrel are in a relaxed condition to allow the segmented mandrel to become very flexible. Once the catheter is in proper position within the tubular vessel, tension can be applied to one or more wires of the segmented mandrel to allow it to form a curved structure that matches with the appropriate curve found in the tubular member of the body. A catheter can then be advanced over the curved segmented mandrel in a manner described in FIGS. 26-29 to enable the catheter to undergo the curve or curves found in the tubular channel. Once the catheter has found its proper location, the wire or wires of the segmented mandrel can be released of tension causing the mandrel to become very flexible and easily removed. The remaining catheter is then available for a diagnostic or a therapeutic delivery.

It is understood that the present invention is not limited to the specific embodiments presented herein. Also combinations of embodiments are envisioned. This invention is further understood to have applications that extend far beyond simply the carotid therapy and vascular therapy. The catheter can find applications in any tubular member of the body including veins, intestines, esophagus, trachea, and other tubular members. It is particularly applicable to tubular members that require a catheter to make a significant turn and head back in a direction that is almost the same direction from which it originated.

| REFERENCE NUMERALS IN DRAWINGS | |
| --- | --- |
| 5 | Access guide catheter |
| 10 | Catheter shaft |
| 15 | Fiber |

REFERENCE NUMERALS IN DRAWINGS

| | |
|---|---|
| 20 | Proximal end of catheter |
| 25 | Fiber lumen |
| 27 | Contained region |
| 30 | Proximal region of catheter |
| 35 | Opening |
| 37 | Wall of catheter |
| 40 | Proximal end of loop region |
| 45 | Loop Region |
| 50 | Attachment point |
| 55 | Distal region of catheter |
| 57 | Distal end of catheter |
| 60 | Locking element |
| 65 | Manifold |
| 70 | Tensioning element |
| 75 | Access lumen |
| 80 | External sheath |
| 85 | Guidewire |
| 90 | Sheath |
| 95 | Closed loop |
| 100 | Steerable sheath |
| 105 | Stiff region of sheath |
| 110 | Flexible region of sheath |
| 115 | Tension cord |
| 120 | Cord lumen |
| 125 | Catheter body |
| 130 | Cord attachment |
| 135 | Tensioning element |
| 140 | Manifold |
| 145 | Tension direction |
| 150 | Hook shape |
| 155 | Curved region |
| 160 | Access lumen |
| 165 | Tension lock |
| 200 | Guidewire |
| 205 | Filterwire |
| 210 | Filter |
| 215 | Lesion |
| 220 | Everted wire loop |
| 235 | Shaped guide catheter |
| 240 | Shaped catheter shaft |
| 245 | Curved region |
| 250 | Marker line |
| 255 | Distal region |
| 260 | Neck region |
| 265 | Proximal region |
| 270 | Sheath |
| 275 | Guidewire |
| 280 | Stiffening mandrel |
| 282 | Tubular stiffening mandrel |
| 285 | Distal region of mandrel |
| 287 | Proximal region of mandrel |
| 290 | Sheath manifold |
| 295 | Shaped guide manifold |
| 300 | Junction of mandrel |
| 305 | Proximal end of curved region |
| 310 | Distal end of curved region |
| 312 | Access guide with loop |
| 315 | Steering fiber |
| 320 | Cinch fiber |
| 322 | Tubular shaft |
| 325 | Distal region of guide |
| 330 | Loop region |
| 340 | Fiber lumen |
| 345 | Contained region |
| 347 | Control end of steering fiber |
| 350 | Control element |
| 355 | Manifold |
| 360 | Fiber opening |
| 370 | Stop element |
| 372 | Steering orifice |
| 375 | Access lumen |
| 380 | Attachment point |
| 385 | Distal end of loop region |
| 395 | Distal end, flexible distal region |
| 397 | Tension element for cinch fiber |
| 399 | Closed loop |
| 400 | Removal end of steering fiber |
| 405 | Guidewire |
| 410 | Flexible region |
| 415 | Tapered sheath |
| 417 | Contrast inlet |
| 418 | Sheath lumen |
| 420 | Guidewire |
| 425 | Beveled recess |
| 430 | Tapered distal end |
| 435 | Perfusion holes |
| 440 | Access catheter |
| 445 | Tip region |
| 450 | Stiffer region |
| 455 | Proximal region |
| 460 | Loop region |
| 470 | Attachment point |
| 475 | Proximal fiber opening |
| 480 | Distal region |
| 485 | Distal end of catheter |
| 490 | Steering fiber |
| 495 | Control end of steering fiber |
| 500 | Access lumen |
| 505 | Fiber lumen |
| 510 | Distal end of stiffer region |
| 515 | Distal fiber opening |
| 520 | Steering orifice |
| 525 | Stop element |
| 527 | Removal end of steering fiber |
| 530 | Cinch fiber |
| 535 | Proximal end of stiffer region |
| 540 | Guidewire |
| 545 | Closed loop region |
| 550 | Access guide catheter |
| 555 | Guidewire |
| 560 | Fiber |
| 565 | Loop region |
| 570 | Tapered sheath |
| 575 | Attachment point |
| 580 | Fiber opening |
| 585 | Closed loop |
| 590 | Distal region |
| 595 | Rapid exchange access guide |
| 600 | Proximal element |
| 605 | Distal guide segment |
| 610 | Steering fiber |
| 615 | Manifold |
| 620 | Distal fiber opening |
| 625 | Steering orifice |
| 630 | Stop element |
| 635 | Cinch fiber |
| 640 | Attachment point |
| 645 | Proximal fiber opening |
| 650 | Proximal opening to guide |
| 655 | Contrast dye lumen |
| 660 | Braided structure |
| 665 | Thin overlap |
| 670 | Fiber opening |
| 672 | Access guide catheter |
| 675 | Distal region |
| 680 | Loop region |
| 682 | Control end of common fiber |
| 685 | Common fiber |
| 687 | Catheter shaft |
| 690 | Fiber opening |
| 695 | Opening B |
| 700 | Distal end of catheter |
| 705 | Loop B |
| 710 | Opening C |
| 715 | Loop C |
| 720 | Permanent attachment D |
| 725 | Stop element |
| 732 | Removal end of common fiber |
| 735 | Cinch release member |
| 740 | Release attachment C |
| 745 | Release attachment B |
| 750 | Closed loop |
| 755 | Steering holding member |
| 760 | Loop E |
| 765 | Loop F |
| 770 | Opening F |

-continued

| REFERENCE NUMERALS IN DRAWINGS | |
|---|---|
| 775 | Opening E |
| 780 | Steering release member |
| 785 | Releasable interlock E |
| 790 | Releasable interlock F |
| 795 | Single contiguous fiber |
| 800 | Segmented mandrel |
| 805 | Segment |
| 810 | Circular tube |
| 815 | Trapezoidal segment |
| 820 | Parallelogram segment |
| 825 | Hypotube 1 |
| 830 | Hypotube 2 |
| 835 | Joint |
| 840 | Wire 1 |
| 845 | Wire 2 |
| 847 | Guidewire lumen |
| 850 | Distal segment |
| 855 | Wire attachment |
| 860 | Wire 1 tensioner |
| 865 | Wire 2 tensioner |
| 870 | Access catheter |
| 872 | First curve |
| 875 | Distal portion of segmented mandrel |
| 880 | Second curve |
| 885 | Proximal mandrel |
| 890 | Guidewire |
| 892 | Loop curve |
| 895 | Flexible region of catheter |
| 900 | Stiffer region of catheter |
| 905 | Cinch fiber |
| 910 | Closed loop |

We claim:

1. A guide catheter for providing access to a vessel of the body for passage of an interventional catheter therethrough comprising;
   A. a hollow tubular member having a tensioning element at its proximal end and having a portion of said hollow tubular member that is formable into a loop region, said hollow tubular member having an open distal end, and an access lumen extending from said proximal end to said distal end,
   B. a fiber forming at least one attachment point to said distal end of said loop region at one or more locations and extending through at least one fiber opening proximal to said fiber attachment point,
   C. said tensioning element being able to apply and hold tension to said fiber to form said hollow tubular member into a closed loop in said loop region by placing said fiber attachment point into close approximation with said fiber opening,
   D. at least one of said fiber attachment points or said fiber openings holds said fiber via releasable attachments that encircle said fiber, said releasable attachments being able to be opened to release said fiber and provide translation of location of said closed loop along said hollow tubular member.

2. The guide catheter of claim 1 wherein said fiber opening extends through a side opening in the wall of said hollow tubular member proximal to said fiber attachment point.

3. The guide catheter of claim 1 wherein said fiber opening consists of the distal end of an external sheath placed around said hollow tubular member and movable along the axis of said hollow tubular member.

4. The guide catheter of claim 1 wherein all but one of said fiber attachment points are releasable fiber attachment points formed of looped releasable attachments that are held in a closed configuration, the closed configuration being able to form an open configuration to enable said attachment point to translate its location along said hollow tubular member.

5. The catheter of claim 4 wherein said releasable fiber attachment points are held in the closed configuration by a release member, said release member being removable to release said releasable fiber attachment points.

6. The catheter of claim 5 wherein said release member is a portion of a second fiber.

7. The guide catheter of claim 1 wherein said fiber openings located along said hollow tubular member hold said fiber via releasable attachments that encircle said fiber, said releasable attachments being able to be opened to release said fiber and provide translation of location of said fiber attachment along said hollow tubular member.

8. The catheter of claim 7 wherein said releasable attachments are released by a release member that allows said releasable attachments to no longer encircle said fiber.

9. The guide catheter of claim 1 wherein all but one of said fiber opening are releasable fiber openings that enable said fiber openings to interact consecutively along said hollow tubular member.

10. The guide catheter of claim 1 further comprising a distal region of said hollow tubular member distal to said loop region, said distal region having said fiber releasably attached to said distal region.

11. The guide catheter of claim 1 wherein said loop region has a hollow tubular member diameter to provide passage of a therapeutic catheter therethrough and a proximal region is significantly smaller in diameter and allows adjacent space within the body vessel for a therapeutic catheter thereby providing a rapid exchange guide catheter.

12. The guide catheter of claim 11 wherein said hollow tubular member has a diameter that is expandable from a first smaller diameter of said hollow tubular member during entry into the body vessel to a larger second diameter after delivery to the body vessel.

13. The guide catheter of claim 1 wherein a lumen of said guide catheter provides passage for a segmented mandrel; said segmented mandrel being comprised of individual segments, said segmented mandrel extending within the access lumen of said hollow tubular member and extending through said open distal end of said hollow tubular member.

* * * * *